United States Patent
Bourang et al.

(10) Patent No.: US 10,624,739 B2
(45) Date of Patent: *Apr. 21, 2020

(54) HEART VALVE DELIVERY SYSTEM WITH VALVE CATHETER

(71) Applicant: Edwards Lifesciences Corporation, Irvine, CA (US)

(72) Inventors: Henry Bourang, Irvine, CA (US); Thanh Huy Le, Oceanside, CA (US); David M. Taylor, Lake Forest, CA (US); Sam Sok, Santa Ana, CA (US); Mario M. Gabriel Iobbi, Westlake Village, CA (US); David J. Evans, Irvine, CA (US); Rajesh A. Khanna, Morrisdale (CA)

(73) Assignee: Edwards Lifesciences Corporation, Irvine, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/833,853

(22) Filed: Dec. 6, 2017

(65) Prior Publication Data
US 2018/0125643 A1    May 10, 2018

Related U.S. Application Data

(63) Continuation of application No. 15/347,505, filed on Nov. 9, 2016, now Pat. No. 9,839,514, which is a (Continued)

(51) Int. Cl.
A61F 2/24     (2006.01)
A61F 2/958    (2013.01)

(52) U.S. Cl.
CPC ............. *A61F 2/243* (2013.01); *A61F 2/2418* (2013.01); *A61F 2/2433* (2013.01); (Continued)

(58) Field of Classification Search
CPC .............. A61F 2/243; A61F 2002/9583; A61F 2/2427; A61F 2/2436; A61F 2/2418; A61F 2/2433
See application file for complete search history.

(56) References Cited

U.S. PATENT DOCUMENTS 3,409,013 A    11/1968    Berry
3,587,115 A    6/1971    Shiley
(Continued)

FOREIGN PATENT DOCUMENTS

DE    19532846 A1    3/1997
DE    19546692 A1    6/1997
(Continued)

*Primary Examiner* — Shaun L David
*Assistant Examiner* — Christina C Lauer
(74) *Attorney, Agent, or Firm* — Klarquist Sparkman LLP

(57) ABSTRACT

An assembly for treating a native valve in a human heart includes a prosthetic heart valve having an expandable frame and a valvular structure. The assembly also includes a tubular sleeve and a valve catheter disposed within the sleeve. A plurality of metal extension arms are coupled to the valve catheter for holding the prosthetic heart valve. The extension arms are configured to radially expand with the prosthetic heart valve during expansion of the prosthetic heart valve at a treatment site. A plurality of metal rods extend distally from the valve catheter. The rods are axially movable relative to the extension arms. A plurality of release members are provided for releasing the prosthetic heart valve from the extension arms upon movement of the metal rods.

7 Claims, 27 Drawing Sheets

Related U.S. Application Data continuation of application No. 14/561,113, filed on Dec. 4, 2014, now Pat. No. 9,539,092, which is a continuation of application No. 13/449,200, filed on Apr. 17, 2012, now abandoned, which is a continuation of application No. 11/252,657, filed on Oct. 18, 2005, now Pat. No. 8,167,932.

(52) U.S. Cl.
CPC .......... *A61F 2/2436* (2013.01); *A61F 2/2439* (2013.01); *A61F 2002/9583* (2013.01)

(56) References Cited

U.S. PATENT DOCUMENTS

| | | |
|---|---|---|
| 3,671,979 A | 6/1972 | Moulopoulos |
| 4,035,849 A | 7/1977 | Angell et al. |
| 4,056,854 A | 11/1977 | Boretos et al. |
| 4,592,340 A | 6/1986 | Boyles |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,922,905 A | 5/1990 | Strecker |
| 4,994,077 A | 2/1991 | Dobben |
| 5,059,177 A | 10/1991 | Towne et al. |
| 5,085,635 A | 2/1992 | Cragg |
| 5,089,015 A | 2/1992 | Ross |
| 5,167,628 A | 12/1992 | Boyles |
| 5,332,402 A | 7/1994 | Teitelbaum |
| 5,370,685 A | 12/1994 | Stevens |
| 5,397,351 A | 3/1995 | Pavcnik et al. |
| 5,411,552 A | 5/1995 | Andersen et al. |
| 5,433,723 A | 7/1995 | Lindenberg et al. |
| 5,545,209 A | 8/1996 | Roberts et al. |
| 5,554,185 A | 9/1996 | Block et al. |
| 5,591,195 A | 1/1997 | Taheri et al. |
| 5,599,305 A | 2/1997 | Hermann et al. |
| 5,639,274 A | 6/1997 | Fischell et al. |
| 5,683,451 A * | 11/1997 | Lenker ............... A61F 2/07 606/198 |
| 5,728,068 A | 3/1998 | Leone et al. |
| 5,749,890 A | 5/1998 | Shaknovich |
| 5,782,809 A | 7/1998 | Umeno et al. |
| 5,840,081 A | 11/1998 | Andersen et al. |
| 5,855,597 A | 1/1999 | Jayaraman |
| 5,855,601 A | 1/1999 | Bessler et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,042,589 A | 3/2000 | Marianne |
| 6,059,809 A | 5/2000 | Amor et al. |
| 6,152,936 A | 11/2000 | Christy et al. |
| 6,162,208 A | 12/2000 | Hipps |
| 6,168,614 B1 | 1/2001 | Andersen et al. |
| 6,217,585 B1 | 4/2001 | Houser et al. |
| 6,245,102 B1 | 6/2001 | Jayaraman |
| 6,299,637 B1 | 10/2001 | Shaolian et al. |
| 6,302,906 B1 | 10/2001 | Goecoechea et al. |
| 6,379,372 B1 | 4/2002 | Dehdashtian et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,656,213 B2 | 12/2003 | Solem |
| 6,730,118 B2 | 5/2004 | Spenser et al. |
| 6,733,525 B2 | 5/2004 | Yang et al. |
| 6,767,362 B2 | 7/2004 | Schreck |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,797,002 B2 | 9/2004 | Spence et al. |
| 6,821,297 B2 | 11/2004 | Snyders |
| 6,830,584 B1 | 12/2004 | Seguin |
| 6,830,585 B1 | 12/2004 | Artof et al. |
| 6,866,650 B2 | 3/2005 | Stevens et al. |
| 6,872,223 B2 | 3/2005 | Roberts et al. |
| 6,893,460 B2 | 5/2005 | Spenser et al. |
| 6,908,481 B2 | 6/2005 | Cribier |
| 6,951,571 B1 | 10/2005 | Srivastava |
| 6,989,028 B2 | 1/2006 | Lashinski et al. |
| 7,018,406 B2 | 3/2006 | Seguin et al. |
| 7,018,408 B2 | 3/2006 | Bailey et al. |
| 7,147,663 B1 | 12/2006 | Berg et al. |
| 7,186,265 B2 | 3/2007 | Sharkawy et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,220 B2 | 6/2008 | Macoviak et al. |
| 7,393,360 B2 | 7/2008 | Spenser et al. |
| 7,429,269 B2 | 9/2008 | Schwammenthal et al. |
| 7,510,575 B2 | 3/2009 | Spenser et al. |
| 7,524,330 B2 | 4/2009 | Berreklouw |
| 7,585,321 B2 | 9/2009 | Cribier |
| 7,618,446 B2 | 11/2009 | Andersen et al. |
| 7,785,366 B2 | 8/2010 | Maurer et al. |
| 8,029,556 B2 | 10/2011 | Rowe |
| 8,167,932 B2 | 5/2012 | Bourang |
| 8,449,606 B2 | 5/2013 | Eliasen et al. |
| 9,839,514 B2 * | 12/2017 | Bourang ............... A61F 2/2433 |
| 2001/0002445 A1 | 5/2001 | Vesely |
| 2001/0007956 A1 | 7/2001 | Letac et al. |
| 2002/0029014 A1 | 3/2002 | Jayaraman |
| 2002/0032481 A1 | 3/2002 | Gabbay |
| 2002/0138138 A1 | 9/2002 | Yang |
| 2002/0198563 A1 | 12/2002 | Gainor et al. |
| 2003/0050694 A1 | 3/2003 | Yang et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125805 A1 | 7/2003 | Johnson et al. |
| 2003/0199963 A1 | 10/2003 | Tower et al. |
| 2003/0212410 A1 | 11/2003 | Stenzel et al. |
| 2004/0039436 A1 | 2/2004 | Spenser et al. |
| 2004/0093060 A1 | 5/2004 | Seguin et al. |
| 2004/0097788 A1 | 5/2004 | Mourlas et al. |
| 2004/0111096 A1 | 6/2004 | Tu et al. |
| 2004/0122516 A1 | 6/2004 | Fogarty et al. |
| 2004/0133263 A1 | 7/2004 | Dusbabek et al. |
| 2004/0133273 A1 | 7/2004 | Cox |
| 2004/0167573 A1 | 8/2004 | Williamson et al. |
| 2004/0167620 A1 | 8/2004 | Ortiz et al. |
| 2004/0186563 A1 * | 9/2004 | Lobbi ............... A61F 2/2418 623/2.11 |
| 2004/0186565 A1 | 9/2004 | Schreck |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0225353 A1 | 11/2004 | McGuckin et al. |
| 2004/0225354 A1 | 11/2004 | Allen et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0060029 A1 | 3/2005 | Le et al. |
| 2005/0075584 A1 | 4/2005 | Cali |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua et al. |

(56) References Cited

U.S. PATENT DOCUMENTS

| | | |
|---|---|---|
| 2005/0131438 A1 | 6/2005 | Cohn |
| 2005/0137686 A1 | 6/2005 | Salahieh et al. |
| 2005/0137692 A1 | 6/2005 | Haug et al. |
| 2005/0137695 A1 | 6/2005 | Salahieh et al. |
| 2005/0137701 A1 | 6/2005 | Salahieh et al. |
| 2005/0143809 A1 | 6/2005 | Salahieh et al. |
| 2005/0187616 A1 | 8/2005 | Realyvasquez |
| 2005/0203549 A1 | 9/2005 | Realyvasquez |
| 2005/0203614 A1 | 9/2005 | Forster et al. |
| 2005/0203617 A1 | 9/2005 | Forster et al. |
| 2005/0222674 A1 | 10/2005 | Paine |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0251157 A1 | 11/2005 | Saadat et al. |
| 2005/0283231 A1 | 12/2005 | Haug et al. |
| 2006/0004439 A1 | 1/2006 | Spenser et al. |
| 2006/0009841 A1 | 1/2006 | McGuckin et al. |
| 2006/0025857 A1 | 2/2006 | Bergheim et al. |
| 2006/0074485 A1 | 4/2006 | Realyvasquez |
| 2007/0005131 A1 | 1/2007 | Taylor |
| 2007/0016286 A1 | 1/2007 | Herrmann et al. |
| 2007/0027518 A1 | 2/2007 | Case et al. |
| 2007/0203575 A1 | 8/2007 | Forster et al. |
| 2007/0265700 A1 | 11/2007 | Eliasen et al. |
| 2008/0125853 A1 | 5/2008 | Bailey et al. |
| 2008/0294230 A1 | 11/2008 | Parker |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0198347 A1 | 8/2010 | Zakay et al. |
| 2011/0015729 A1 | 1/2011 | Jimenez et al. |
| 2012/0123529 A1 | 5/2012 | Levi et al. |
| 2013/0317598 A1 | 11/2013 | Rowe et al. |

FOREIGN PATENT DOCUMENTS

| | | |
|---|---|---|
| DE | 19907646 A1 | 8/2000 |
| DE | 10049812 A1 | 4/2002 |
| DE | 10049814 A1 | 4/2002 |
| EP | 0592410 A1 | 4/1994 |
| EP | 0850607 A1 | 7/1998 |
| EP | 1057460 A1 | 12/2000 |
| EP | 1356793 A2 | 10/2003 |
| EP | 1796597 A2 | 6/2007 |
| FR | 2815844 A1 | 5/2002 |
| WO | 91/17720 A1 | 11/1991 |
| WO | 9810713 A2 | 3/1998 |
| WO | 9829057 A1 | 7/1998 |
| WO | 9904728 A1 | 2/1999 |
| WO | 0041652 A1 | 7/2000 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03022183 A1 | 3/2003 |
| WO | 03047468 A1 | 6/2003 |
| WO | 03068302 A3 | 9/2003 |
| WO | 2005004753 A1 | 1/2005 |
| WO | 2005039448 A1 | 5/2005 |
| WO | 2005046528 A1 | 5/2005 |
| WO | 2005062980 A2 | 7/2005 |
| WO | 2005067819 A1 | 7/2005 |
| WO | 2005084595 A1 | 9/2005 |
| WO | 2005102015 A2 | 11/2005 |
| WO | 2006004825 A2 | 1/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2010121076 A2 | 10/2010 |

* cited by examiner

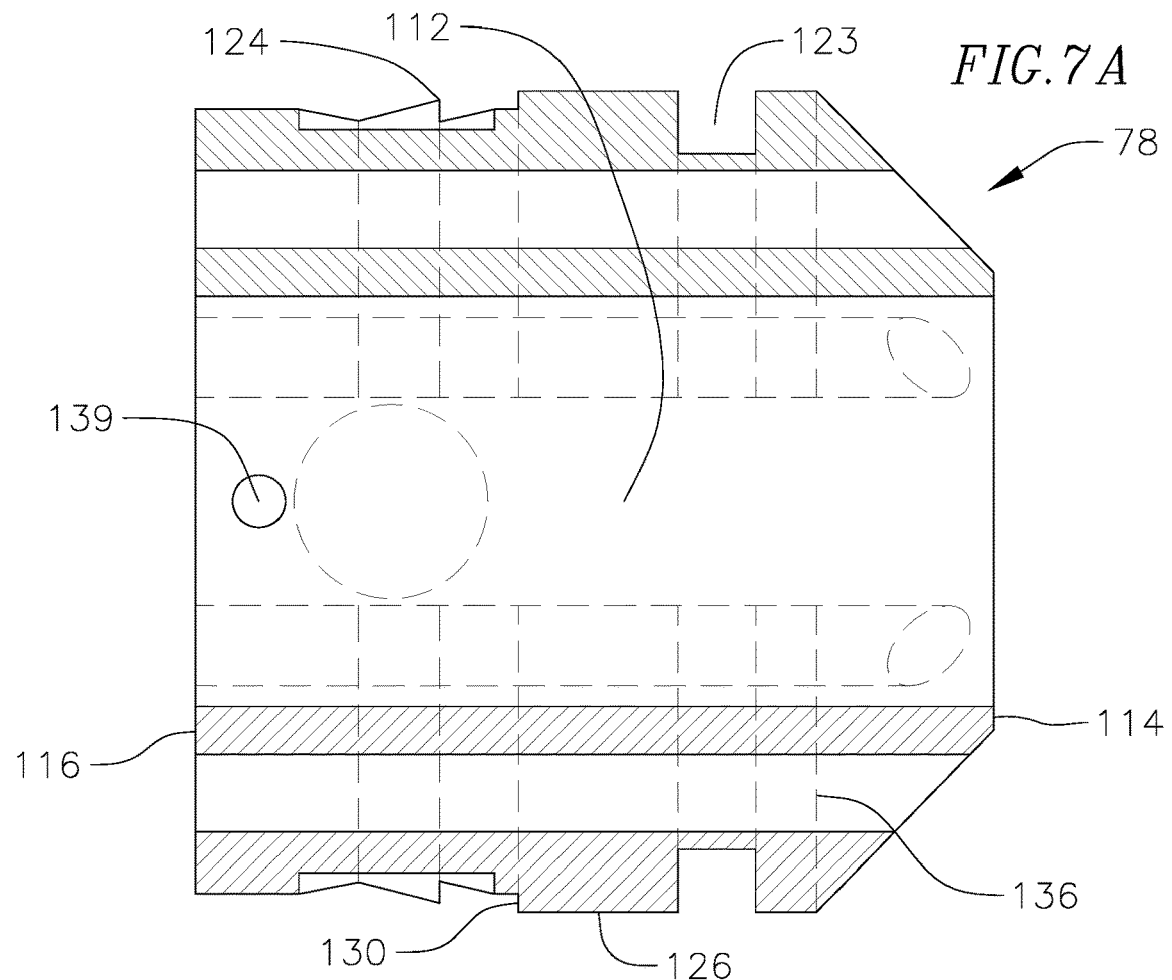
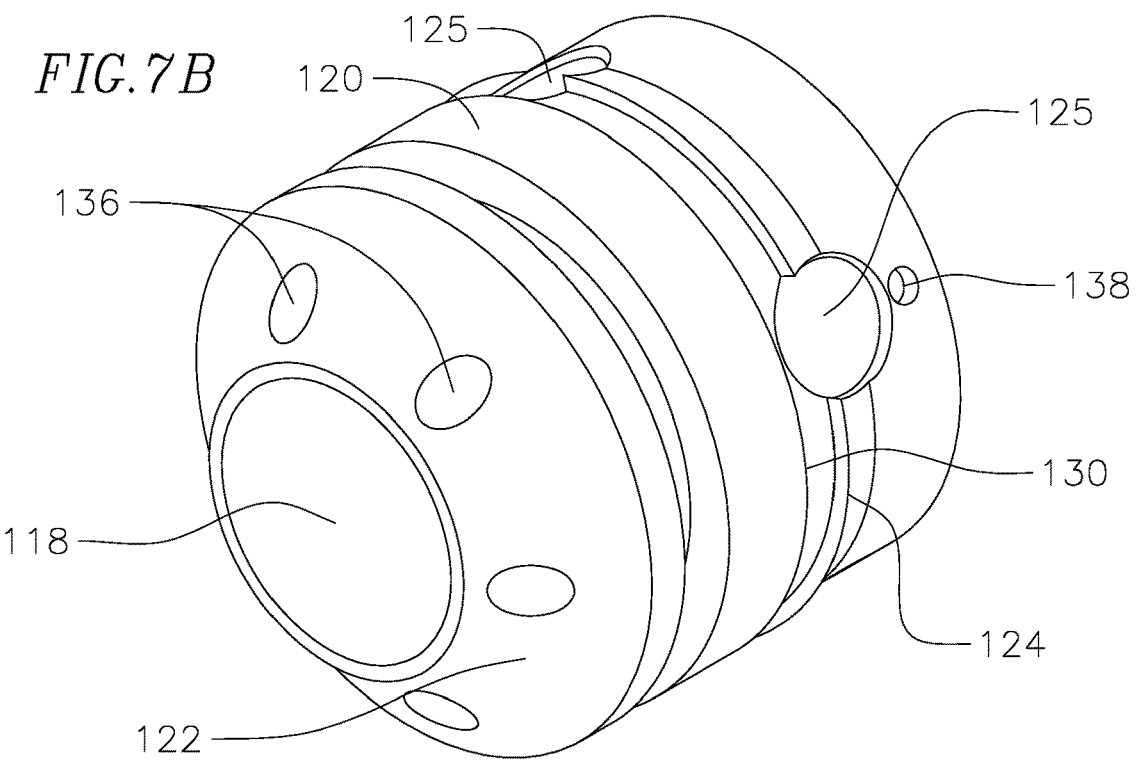

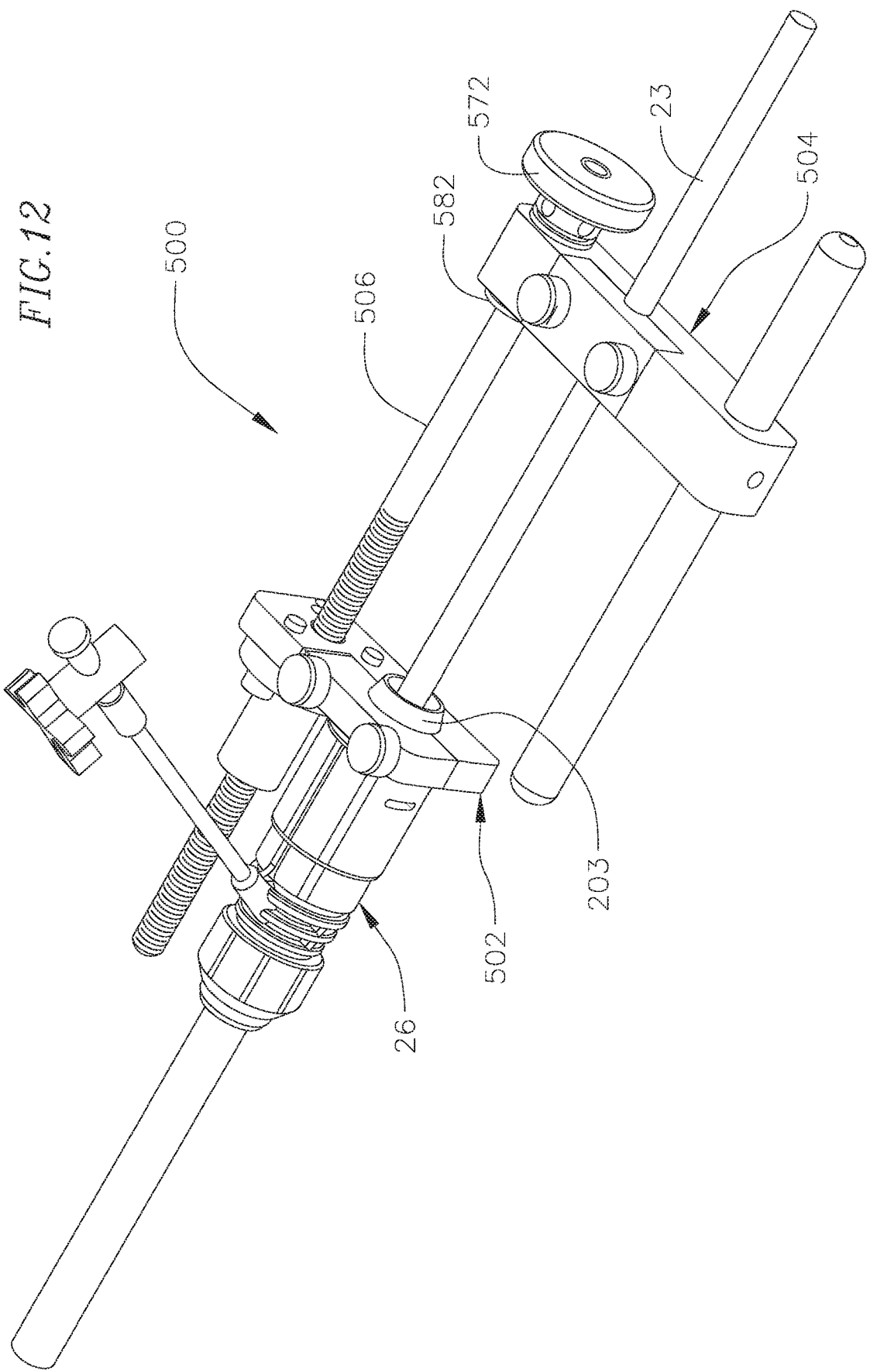

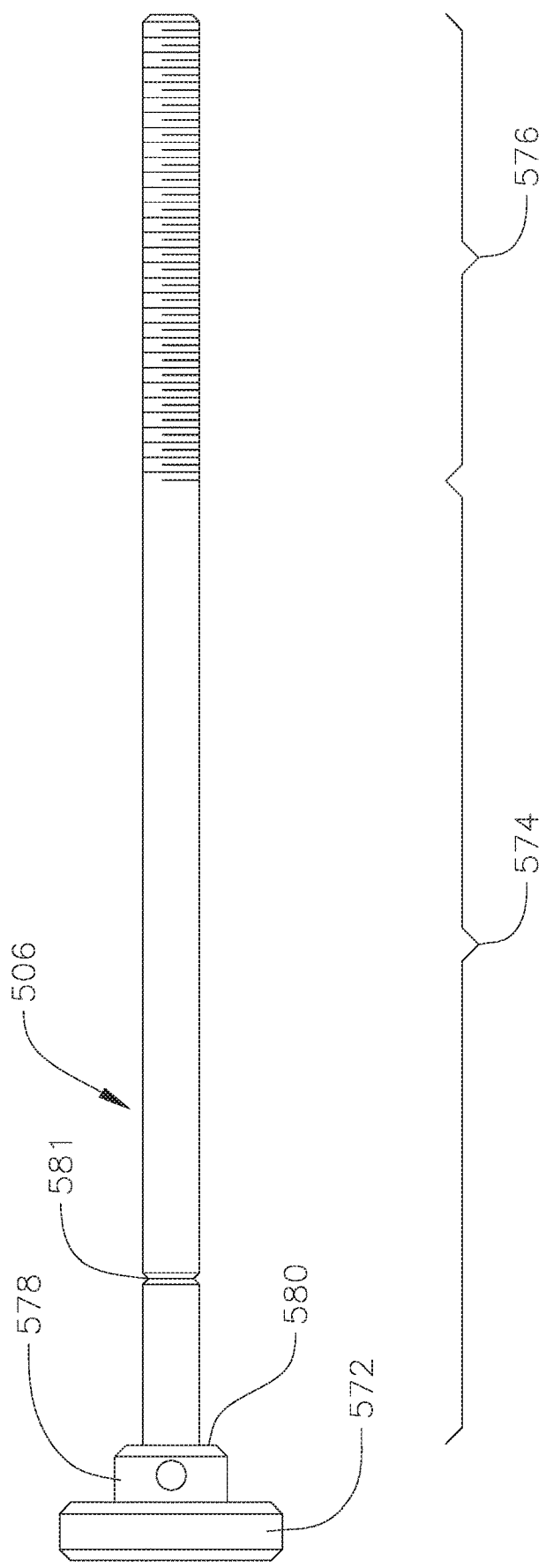

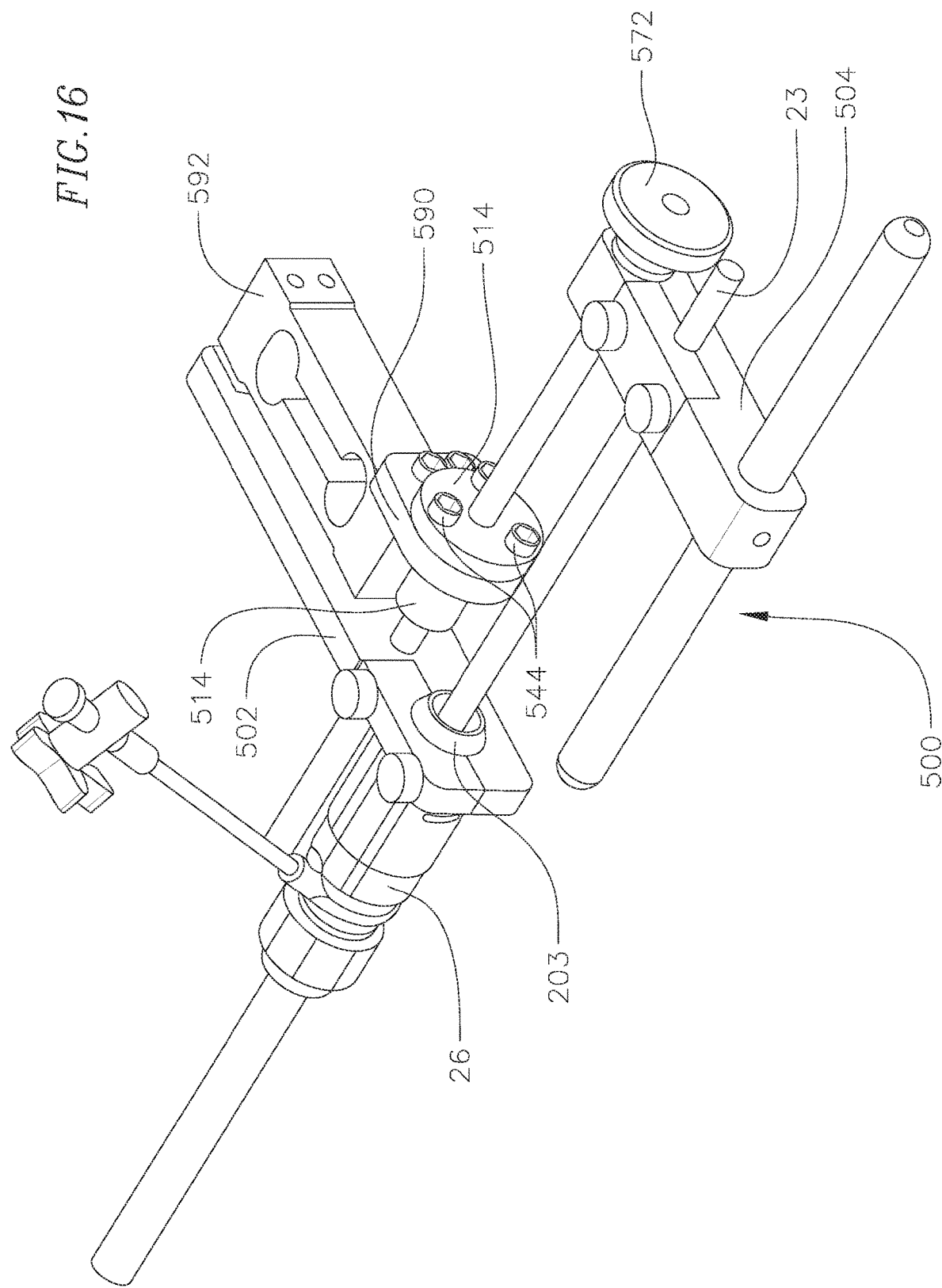

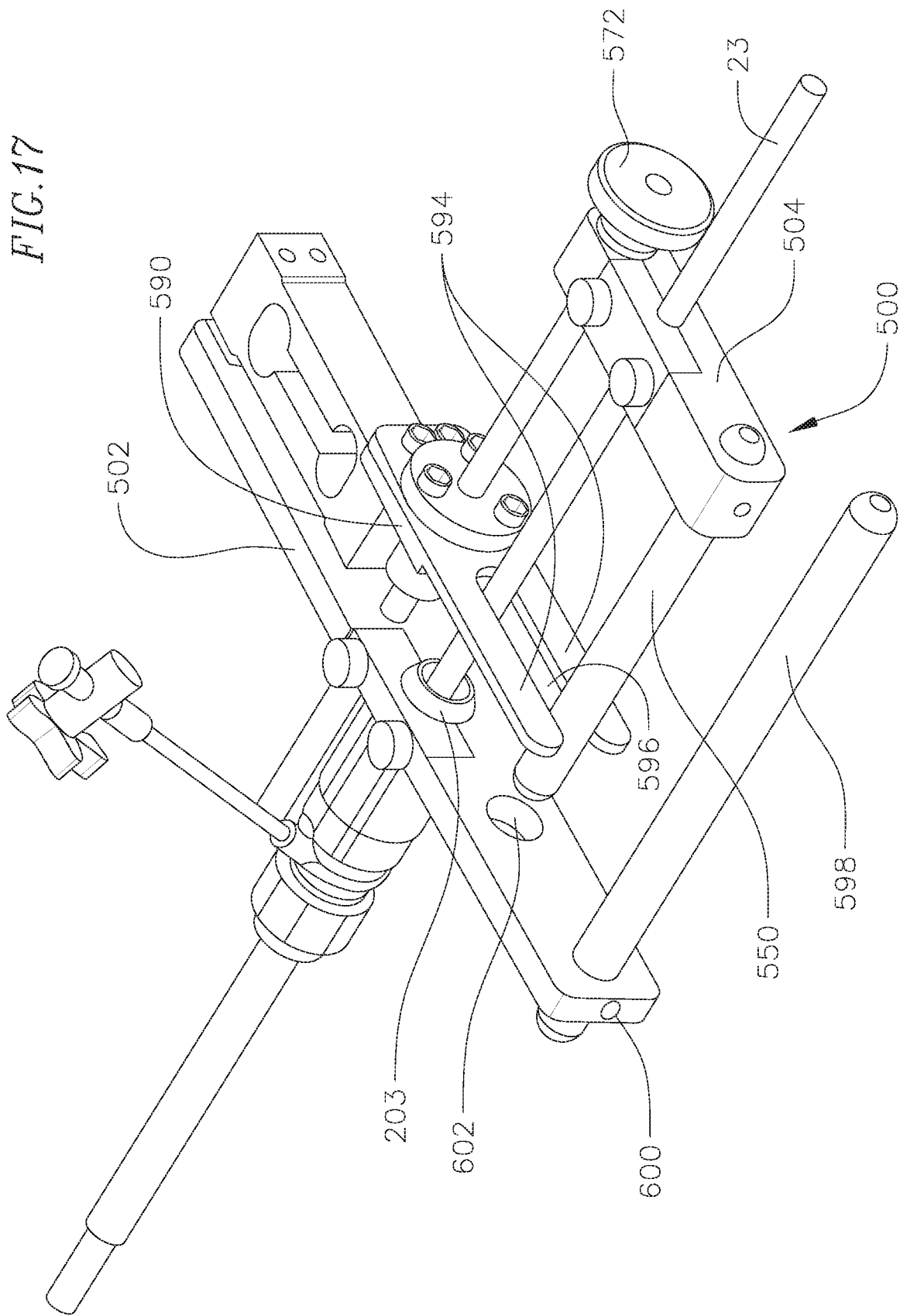

HEART VALVE DELIVERY SYSTEM WITH VALVE CATHETER

RELATED APPLICATIONS

The present application is a continuation of U.S. application Ser. No. 15/347,505, filed Nov. 9, 2016, now U.S. Pat. No. 9,839,514, which is a continuation of U.S. application Ser. No. 14/561,113, filed Dec. 4, 2014, now U.S. Pat. No. 9,539,092, which is a continuation of U.S. application Ser. No. 13/449,200, filed Apr. 17, 2012, now abandoned, which is a continuation of U.S. application Ser. No. 11/252,657, filed Oct. 18, 2005, now U.S. Pat. No. 8,167,932, the entire disclosures of which are incorporated by reference.

FIELD OF THE INVENTION

The present invention generally relates to systems used to deliver medical implants into a human body. More particularly, the present invention is directed to a delivery system for delivering a prosthetic valve to a human heart.

BACKGROUND

Catheter-based procedures are commonly used in medical practice to treat regions within the body that are not easily accessible by surgery or wherein access without surgery is desirable. In one catheter-based procedure, a prosthetic valve is delivered to a human heart using a percutaneous approach for replacing a defective native heart valve. Although the replacement of native heart valves using percutaneously delivered prosthetic valves has shown great potential, the effectiveness of this procedure is often limited by the operator's ability to navigate through the patient's vasculature, such as through small vessels and around the aortic arch.

In one delivery method, a prosthetic valve is mounted on a balloon catheter. Before advancing the prosthetic valve to the heart, a guide sheath is introduced into the iliac artery of the patient. Although the guide sheath adds diameter and complexity to the system, the guide sheath is necessary for advancing the catheter and prosthetic valve through the relatively narrow arterial vessels. The balloon catheter and prosthetic valve are pushed by the operator through the guide sheath to the treatment site. In one shortcoming of this procedure, the balloon catheter may lack the pushability required to be effectively advanced through the guide sheath. Furthermore, after exiting the guide sheath, the prosthetic valve may come into contact with the inner wall of the vessel, such as along the aortic arch. As a result of this contact, the vessel wall may be damaged and advancement of the prosthetic valve may be impeded or prevented altogether. Furthermore, calcification and plaque can be dislodged from the vessel wall.

Due to the shortcomings associated with existing delivery systems, there is a need for a new and improved delivery system that may be used to deliver a prosthetic valve to a human heart in a safe and effective manner. It is desirable that such a system does not require the use of a conventional guide sheath. It is also desirable that such a system eases the tracking process and reduces the displacement of plaque or calcification along the inner walls of the body vessels. It is also desirable that such a system has sufficient flexibility to track through the curves of a body vessel, while providing sufficient pushability to ensure that the prosthetic valve can be tracked to the native valve site. It is desirable that such a system also provides a means for deploying the prosthetic valve at the native valve site in a controlled and precise manner. The present invention addresses this need.

SUMMARY

Preferred embodiments of a system for treating a native valve in a human heart include a delivery sleeve containing a prosthetic valve which enters a vessel without the use of a guide sheath. Entry without the use of a guide sheath is achieved by the gradual profile of a step balloon, the tip of which protrudes from the distal end of the delivery sleeve and provides a smooth transition from a guide wire to the delivery sleeve.

The delivery sleeve is comprised of materials which give the catheter sufficient pushability, rigidity, and flexibility to allow an operator to accurately place the distal end of the catheter at a site where the prosthetic valve is to be deployed. The smooth transition of the step balloon prevents the loosening of calcification and plaque inside the vessel, and particularly in the area of the aortic arch.

Another advantage of the system is the ability to prepare the site of the native valve for implantation of the prosthetic valve. It is advantageous to dilate the stenotic leaflets prior to implanting the prosthetic valve. The leaflets are dilated as the step balloon is deflated, passed through the opening between the leaflets, and then reinflated.

Another advantage of the system is the ability to aid in crossing the site of the native valve for implantation of the prosthetic valve. The step balloon provides a smooth tapered tip that transitions to the sheath for easy crossing of the calcified leaflets.

Yet another advantage of the system is the ability to retract the step balloon through the prosthetic valve after deployment. The tapered tip may be deflated and collapsed to facilitate retraction of the balloon through the prosthetic valve. This feature advantageously reduces or eliminates the possibility of damaging the prosthetic valve leaflets or snagging on the valve frame during retraction.

At the site of valve deployment, the delivery sleeve retracts, allowing full expansion of the step balloon. The distal end of a valve catheter contains flexible extensions which flex outwardly as the balloon inflates. The prosthetic valve is connected to the flexible extensions, thereby providing improved stability and controllability during deployment.

In one aspect, a system for treating a native valve in a human heart comprises a prosthetic valve, valve catheter and tubular delivery sleeve. The prosthetic valve includes an expandable frame and a valvular structure. The tubular sleeve is configured for advancement through a patient's vasculature. The tubular sleeve defines a passageway and the valve catheter is configured for slidable advancement through the passageway. A releasable engagement mechanism is disposed along a distal end portion of the valve catheter for engaging the prosthetic valve. An actuation mechanism is disposed along a proximal end portion of the valve catheter for causing the releasable engagement mechanism to release the prosthetic valve.

In one variation, the releasable engagement mechanism comprises a plurality of flexible extension arms configured to hold the prosthetic valve during expansion of the prosthetic valve at a treatment site. The system may further comprise at least one suture for securing the prosthetic valve to the flexible extension arms. At least one slidable member is attached to the actuation mechanism and extends distally toward the prosthetic valve. The slidable member, such as a wire, is retractable for detaching the suture from the prosthetic valve, thereby releasing the prosthetic valve from the flexible extension arms.

In another variation, the system may further comprise an expandable transition member extending from a distal end of the tubular sleeve. In one variation, the transition member comprises an inflatable balloon having a tapered distal end portion. The inflatable balloon is preferably disposed at least partially within the prosthetic valve such that inflation of the inflatable balloon assists in the expansion of the prosthetic valve. When the system includes an inflatable balloon, the expandable frame of the prosthetic valve may be balloon-expandable or self-expanding. In one variation, an expandable basket may be used in place of an inflatable balloon for providing a dilator or for facilitating expansion of the prosthetic valve.

In another variation, a handle assembly may be provided for controllably retracting the tubular sleeve for exposing the prosthetic valve at the treatment site. In one embodiment, the handle assembly has a distal end portion attached to the tubular sleeve and a proximal end portion attached to the valve catheter. The handle assembly may utilize a lead screw of other suitable mechanism for advancing the valve catheter in a controlled manner and securely holding the relative positions of the valve catheter and tubular sleeve.

In another aspect, a method of deploying a prosthetic valve within a native valve in a human heart is provided. The method includes providing an elongate valve catheter having a releasable attachment mechanism along a distal end portion. The prosthetic valve is attachable to the releasable attachment mechanism. The valve catheter and prosthetic valve are placed in a tubular sleeve. The tubular sleeve, valve catheter and prosthetic valve are advanced as a single unit through a femoral artery and over an aortic arch until the prosthetic valve is substantially located within the native valve. The delivery sleeve is retracted relative to the valve catheter to expose the prosthetic valve and an actuation mechanism on a proximal end of the valve catheter is actuated to release the prosthetic valve from the valve catheter.

In one variation, an inflatable balloon is disposed within the prosthetic valve during advancement of the prosthetic valve. A tapered distal end portion of the inflatable balloon extends from the tubular sleeve for providing a dilator to facilitate advancement through the patient's vasculature. In another variation, the inflatable balloon may be used to dilate the native valve by pushing aside the stenotic leaflets, thereby facilitating insertion of the prosthetic valve into the native valve. In yet another variation, the inflatable balloon may be inflated after retracting the tubular sleeve to facilitate expansion and seat the prosthetic valve within the native valve. In yet another variation, preferred embodiments of the system allow the tubular sleeve to be advanced relative to the valve catheter after exposing the prosthetic valve. Advancement of the tubular sleeve causes the prosthetic valve to collapse again such that it may be repositioned in the event that the initial deployment is not desirable. After repositioning the prosthetic valve, the sleeve may be retracted again and the prosthetic valve may then be released from the valve catheter.

In another aspect, a device for treating a human heart comprises a prosthetic valve, a tubular delivery sleeve having a proximal end, a lead screw nut coupled to the proximal end of the tubular delivery sleeve, and a valve catheter having a distal end configured for releasable attachment to the prosthetic valve, wherein the valve catheter and the prosthetic valve are slidably advanceable through the delivery sleeve. A lead screw is coupled to the valve catheter. The lead screw engages the lead screw nut and rotation of the lead screw causes the valve catheter and the prosthetic valve to advance relative to the delivery sleeve. In one variation, an inflatable balloon is disposed within the prosthetic valve for facilitating expansion of the prosthetic valve within the native valve. The inflatable balloon may have a tapered distal end portion configured to extend from the tubular delivery sleeve. Accordingly, the inflatable balloon may also be used to facilitate advancement through the vasculature and to dilate the stenotic leaflets of the native valve. The tubular delivery sleeve is preferably coated with a hydrophilic coating. In another variation, a plurality of flexible extensions is disposed along the distal end of the valve catheter, the flexible extension being configured for releasable attachment to the prosthetic valve.

BRIEF DESCRIPTION OF THE DRAWINGS

FIGS. 7A and 7B are cross sectional and perspective views, respectively, of a puck of the valve catheter;

FIG. 12 is a perspective view of a handle assembly attached to the delivery system;

FIG. 15 is a side view of a lead screw of the handle assembly;

FIG. 16 is a perspective view of an embodiment of the handle assembly including a load cell;

FIG. 17 is a perspective view of another embodiment of a handle assembly including a load cell;

DETAILED DESCRIPTION

Figure 1:
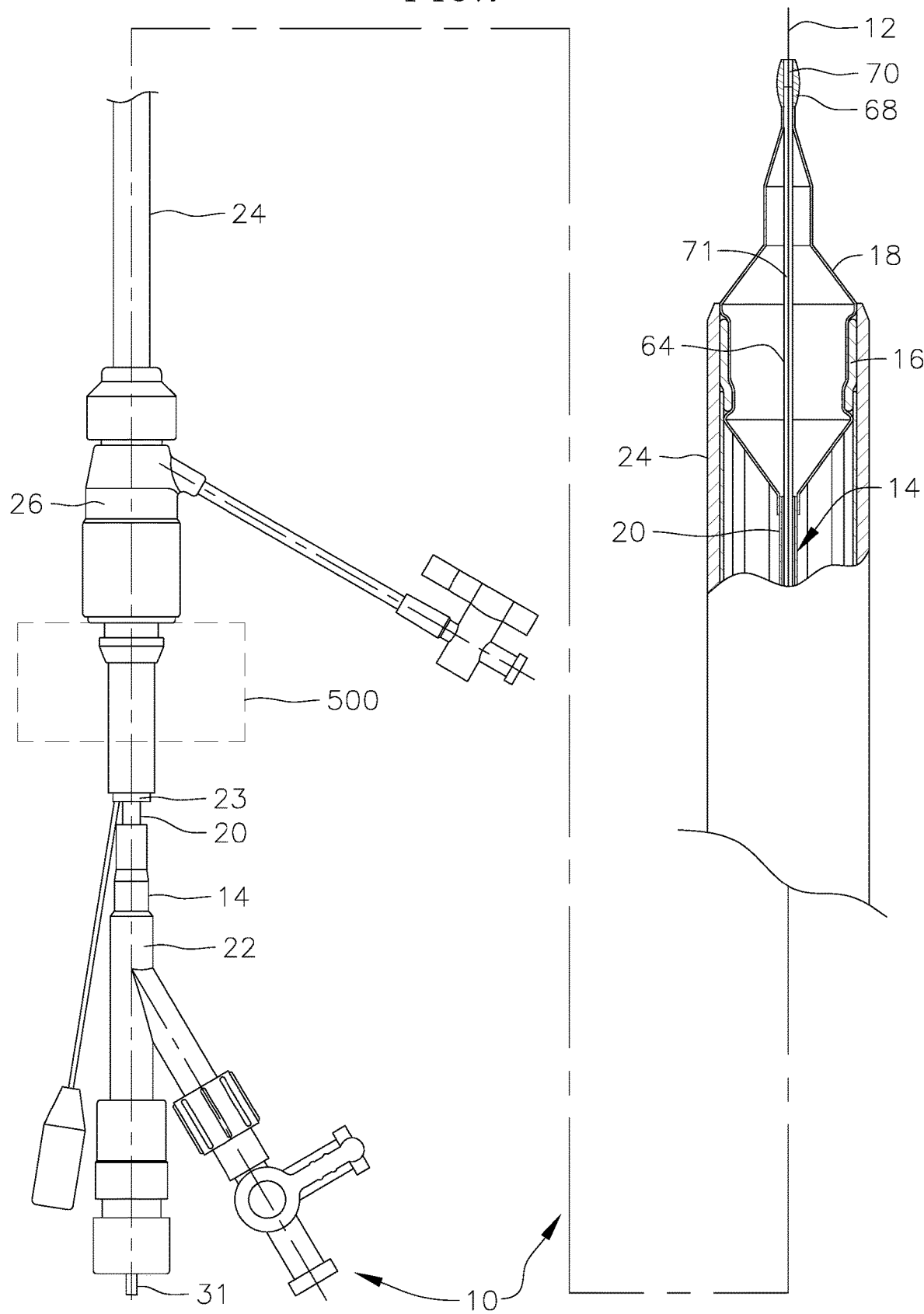
FIG. 1 is a side view of one preferred embodiment of a delivery system according to the present invention with a distal end cut away and shown in cross section.

With reference now to FIG. 1, a heart valve delivery system 10 includes, generally, a guide wire 12 and a balloon catheter 14 having an inflatable balloon 18 located along a distal end portion. An expandable prosthetic valve 16 is located over the inflatable balloon. The balloon catheter 14 also includes an elongate balloon shaft 20, and a support 22 at a proximal end thereof. The balloon shaft 20 of the balloon catheter 14 is received within a valve catheter 23. As will be described in more detail below, the valve catheter 23 is configured for releasable engagement with the prosthetic valve 16. The valve catheter 23 is received within a tubular delivery sleeve 24, with the balloon 18 protruding, at least in part, from a distal end of the delivery sleeve 24. A proximal end of the delivery sleeve 24 is mounted to a proximal hub 26. A handle assembly 500, which will be discussed and depicted in greater detail below, may be attached to the proximal hub 26 of the delivery sleeve 24 to effectuate controlled advancement of the prosthetic valve 16 relative to the delivery sleeve 24.

Figure 2:
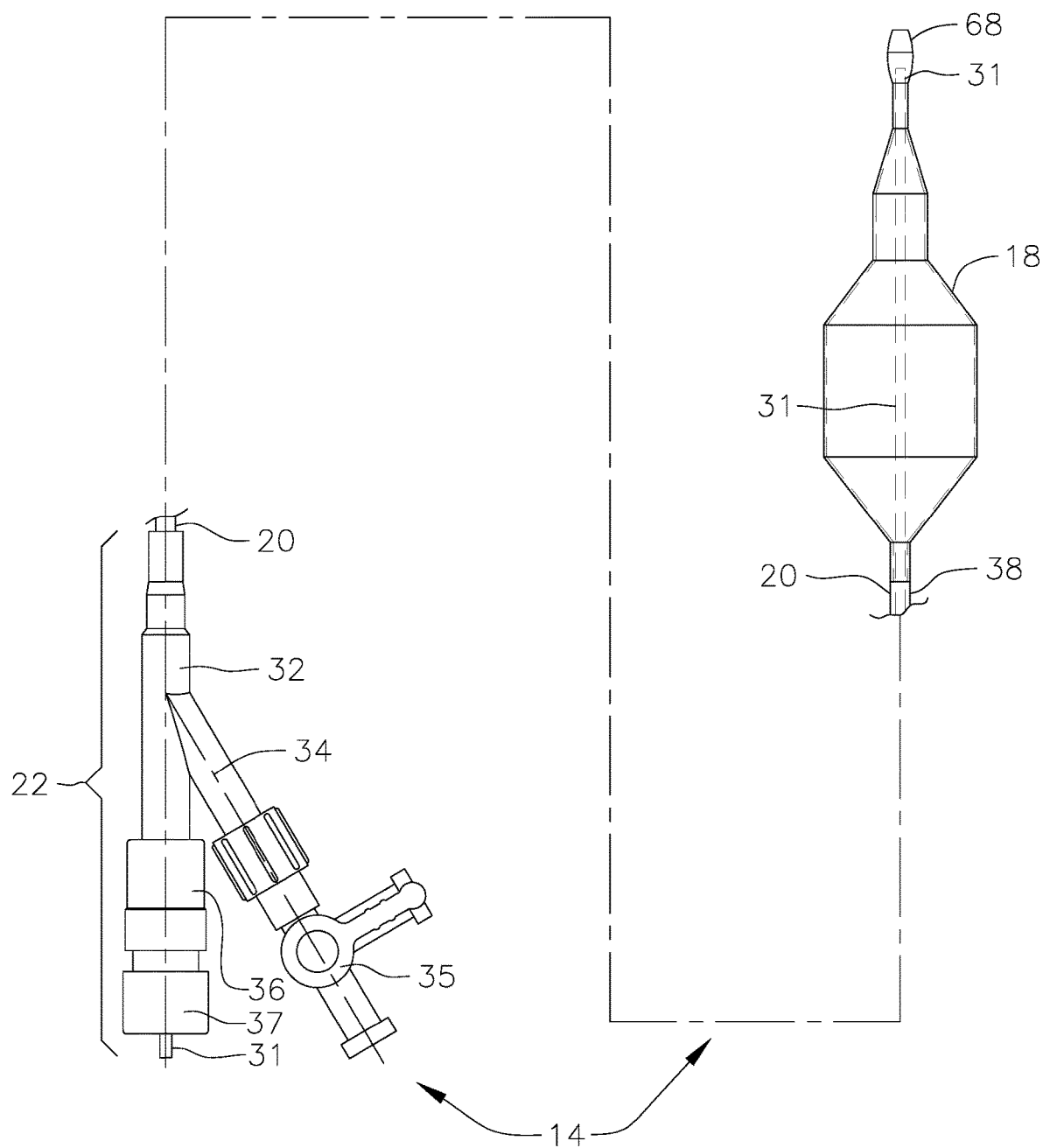
FIG. 2 is a side view of a balloon catheter of the delivery system.

With reference to FIG. 2, the balloon catheter 14 is shown in greater detail. The balloon catheter 14 is provided with a guidewire shaft 31 that defines a guidewire lumen. The support 22 is located along a proximal end of the balloon catheter and includes a main shaft 32 and a fluid shaft 34 extending diagonally from the main shaft 32. A stop cock 35 is located along the fluid shaft 34. The main shaft 32 and the fluid shaft 34 each include a passageway, and the passageways are in communication with one another. A Touhy Borst valve 36, such as described in U.S. Pat. No. 6,592,544, the contents of which are fully incorporated herein by reference, extends proximally from a proximal end of the main shaft 32, and includes a tightening valve 37 at a proximal end thereof. The illustrated balloon shaft 20 is substantially tube shaped and includes an outer surface 38.

In one preferred construction, the balloon catheter 14 is assembled such that the outer surface 38 of the balloon shaft 20 is secured to an inner surface of the main shaft 32 of the support 22. The Touhy Borst valve 36 is placed over the proximal end of main shaft 32 and secured thereto by a threaded connection between the two components. A compression valve inside the Touhy Borst valve 36 surrounds the guidewire shaft 31 and seals an inner passageway in the main shaft 32 of the support 22 from the atmosphere as the tightening valve 37 is tightened.

Figure 3A:
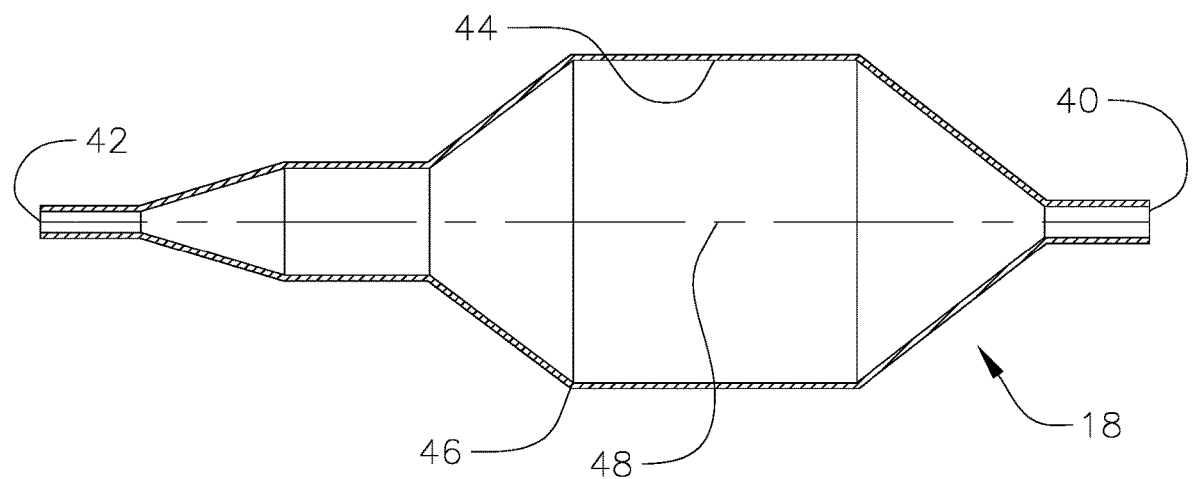
FIGS. 3A and 3B are cross sectional and perspective views, respectively, of a balloon of the balloon catheter.
Figure 3B:
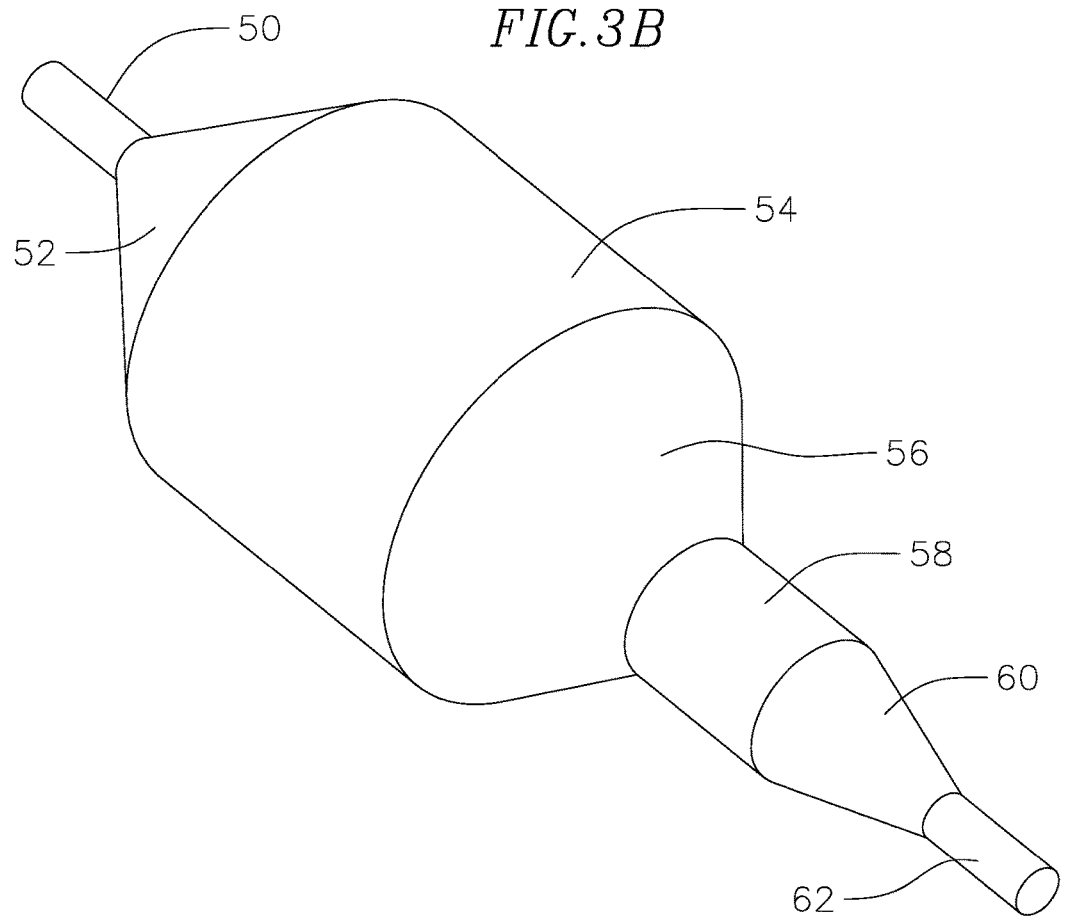

With reference to FIGS. 3A and 3B, the inflatable balloon 18 has a proximal end portion 40 and a distal end portion 42 and includes an inner surface 44, an outer surface 46, and a passageway 48 longitudinally extending therethrough. When viewed from the proximal end portion 40 to the distal end portion 42, the illustrated embodiment of the balloon 18 includes seven regions: a first slender region 50, a first conical region 52, a main cylindrical region 54, a second conical region 56, a secondary cylindrical region 58, a third conical region 60, and a second slender region 62. The balloon 18 is preferably inflated by a fluid, such as saline, and may be formed of any suitable material, such as, for example, nylon. The distal end portion 42 of the balloon 18 is preferably shaped to provide a transition member between the guidewire 12 and the relative large diameter delivery sleeve 24 (as shown in FIG. 1), thereby facilitating advancement of the delivery system through the patient's vasculature. In preferred embodiments, the balloon 18 also provides a dilator tip, thereby eliminating the need for a separate dilator mechanism. The outer surface of the balloon and the delivery sleeve are preferably provided with a lubricious coating. The lubricious coating and the shape of the balloon allow the delivery system (including the prosthetic valve) to be advanced through relatively narrow and or calcified vasculature in a patient. Accordingly, in one advantageous feature, preferred embodiments of the delivery system may be used without a guide sheath.

With reference to FIGS. 1 through 3B, one preferred construction of the balloon 18 will now be described in more detail. The inner surface 44 of first slender portion 50 of the balloon 18 is secured to the outer surface 38 of the balloon shaft 20 at a distal end of the balloon shaft, thus placing the passageway of the balloon shaft 20 in communication with the passageway 48 of the balloon 18. The inner surface 44 of the second slender portion 62 is secured to an outer surface 64 of the guidewire shaft 31. The connection can be achieved by adhesion or by thermal joining, or both. A soft tip 68 having a passageway 70 extending therethrough is secured to the outer surface 64 of the guidewire shaft 31 at a distal end thereof, and extends distally from the guidewire shaft 31, the passageway 70 of the soft tip 68 being in communication with a passageway 71 of the guidewire shaft 31.

Figure 4:
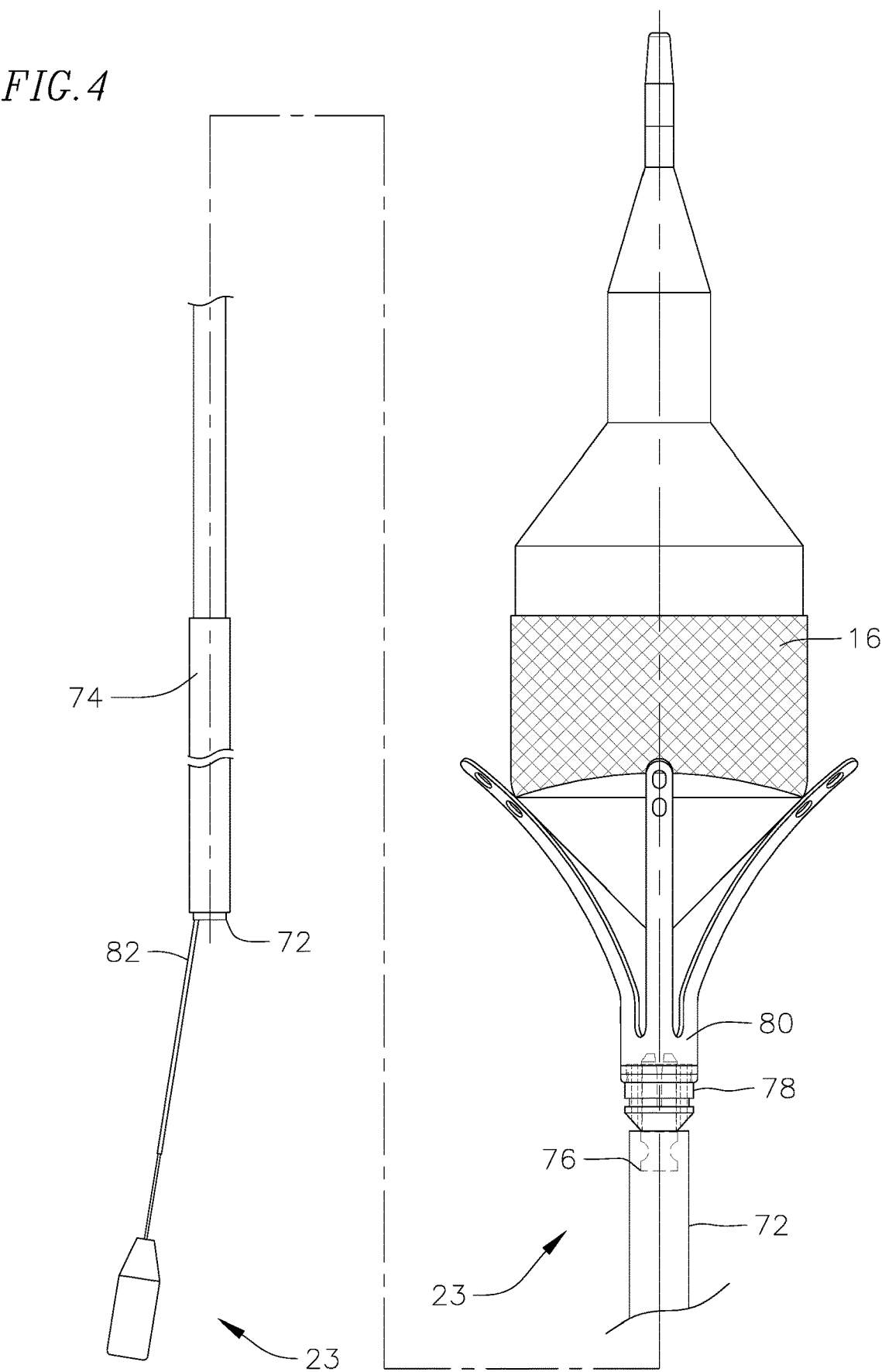
FIG. 4 is a side view illustrating proximal and distal ends of a valve catheter which forms a portion of the delivery system.

With reference to FIGS. 4 through 8, the assembly and function of the valve catheter 23 will now be described. As best shown in FIG. 4, the valve catheter 23 provides a releasable engagement mechanism for holding and releasing the prosthetic valve 16. In the illustrated embodiment, the valve catheter 23 includes a multi-lumen shaft 72, around a proximal portion of which a stiffener tube 74 is disposed. A collet 76 extends from inside a central lumen of the multi-lumen shaft 72 and is snapped into a puck 78. The puck 78 is snapped into the mop 80 such that the mop extends distally from the puck. The valve catheter 23 also includes a wire tube 82 extending proximally from a proximal end of the multi-lumen shaft 72. The valve catheter 23 carries the prosthetic valve 16 to the native heart valve site and facilitates deployment of the prosthetic valve 16, as described below.

Figure 5:
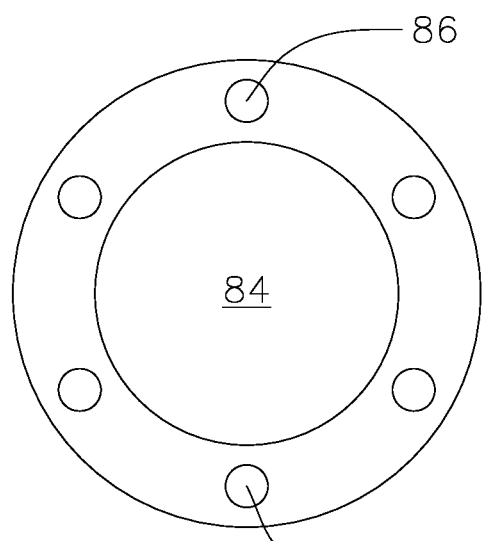
FIG. 5 is a cross sectional view of a multi-shaft lumen of the valve catheter.

With reference to the cross-sectional view of FIG. 5, the multi-lumen shaft 72 is preferably cylindrically shaped and includes a central lumen 84 longitudinally extending therethrough. Six side lumens 86 extend from a proximal end to a distal end of the multi-lumen shaft 72. In one embodiment, the multi-lumen shaft is made of a thermoplastic elastomer such as polyether block amide, known as Pebax®.

Figure 6A:
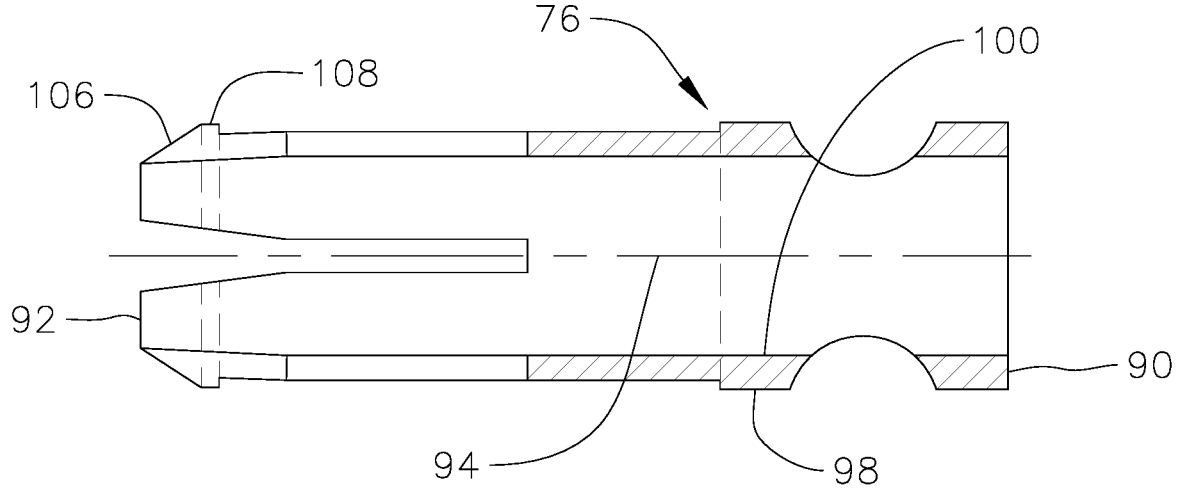
FIGS. 6A and 6B are cross sectional and perspective views, respectively, of a collet of the valve catheter.
Figure 6B:
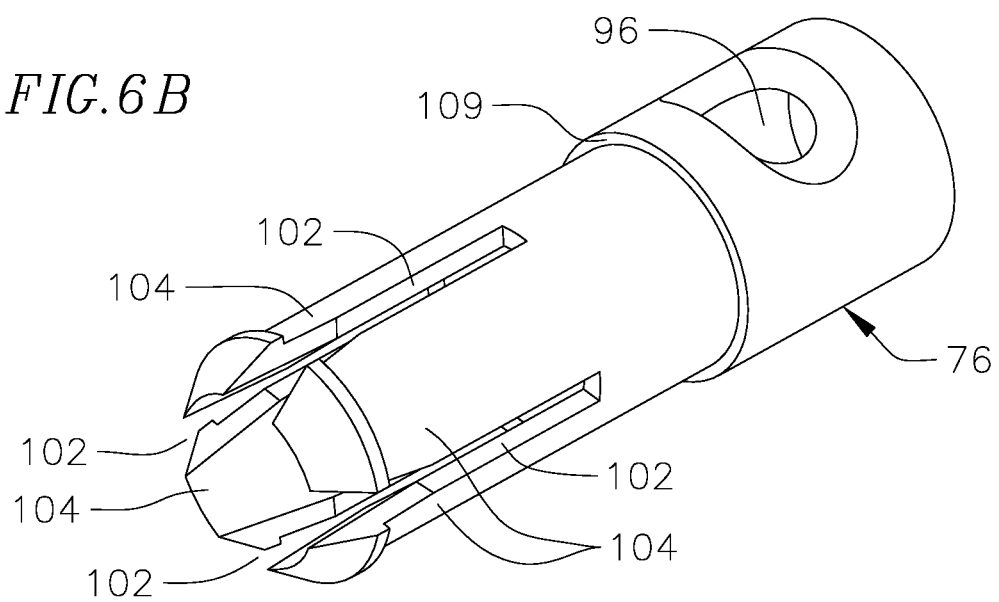

With reference to FIGS. 6A and 6B, the collet 76 is generally cylindrically shaped and includes a proximal end 90 and a distal end 92. A central passageway 94 extends through the collet. Near the proximal end 90, openings 96 extend from an outer surface 98 to an inner surface 100 of the collet 76. Four longitudinal slots 102 pass from the outer surface 98 to the inner surface 100 along the distal end 92 of the collet 76, thereby creating four flexible arms 104. The slots 104 preferably narrow in width from the distal end 92 to the proximal end 90. At the distal end 92 of the collet 76, the outer surface preferably forms an angled surface 106 to facilitate engagement with the puck 78. An annularly shaped flange 108 is located proximally adjacent to the angled surface 106. Along the circumference of the collet 76, the outer surface 98 includes a shoulder surface 109 which extends perpendicular to the outer surface 98 and faces the distal end 92 of the collet 76.

With reference to FIGS. 7A and 7B, the puck 78 is generally tube shaped, having a central lumen 112 extending longitudinally therethrough from a proximal end 114 to a distal end 116. The central lumen 112 is defined by an inner surface 118 of the puck 78. An outer surface 120 of the puck 78 includes an angled portion 122 near the proximal end 114. An annular groove 123 extends around the outer surface of the puck 78 distally adjacent the angled portion 122. Near the distal end 116, the outer surface 120 includes a snap ridge 124 extending around the circumference of the puck 78. The snap ridge 124 is interrupted by four circular indentations 125 which extend from the outer surface 120. The outer surface also includes an annularly shaped flange 126 extending outwardly which defines a shoulder surface 130. Six side lumens 136 extend parallel to the central lumen 112 from the angled portion 122 of the outer surface 120 to the distal end 116 of the puck 78. The side lumens 136 are equally spaced around the circumference of the puck 78. A cylindrically shaped opening 138 extends radially from the outer surface 120 to the inner surface 118 of the puck 78. A pin 139 is inserted into the opening 138, situated flush with the outer surface and protruding inwardly from the inner surface 118 of the puck 78.

Figure 8:
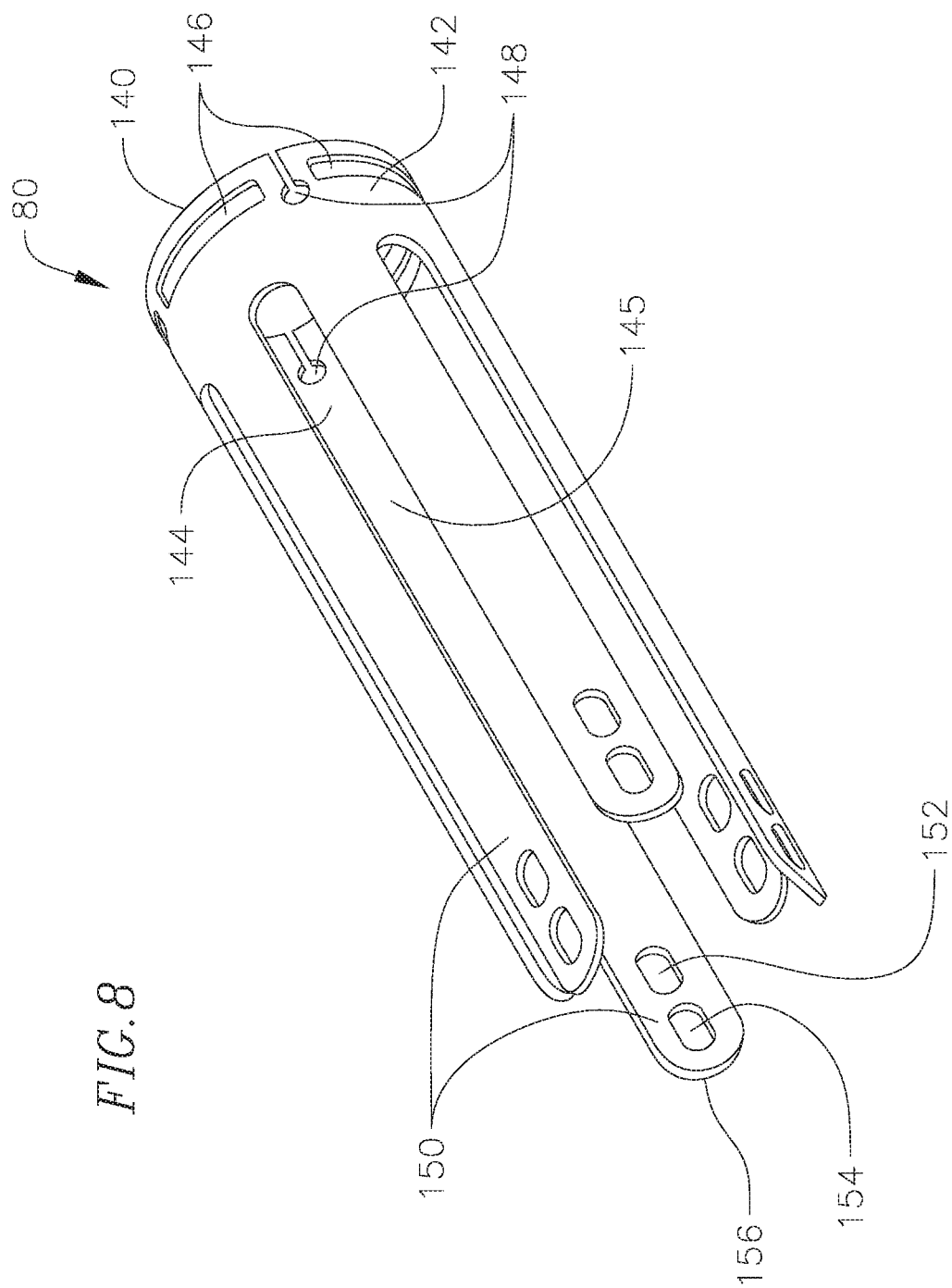
FIG. 8 is a perspective view of a mop of the valve catheter.

With reference to FIG. 8, the mop 80 is generally cylindrical in shape and includes a proximal end 140, an outer surface 142, an inner surface 144, and a passageway 145 extending therethrough. The mop 80 preferably includes six elongate extensions 150 configured for engagement with the prosthetic valve. In one preferred embodiment, the extensions 150 have varying lengths configured for engaging different portions of the prosthetic valve. Each extension preferably includes first and second openings 152, 154 near a distal end 156. Near the proximal end 140 of the mop 80, four openings 146 extend from the outer surface 142 to the inner surface 144, and are aligned along a circumference of the mop 80. Four slots 148 passing from the outer surface 142 to the inner surface 144 extend from the proximal end 140 along the length of the mop 80 and pass between the openings 146. The mop 80 is preferably formed of a shape memory material, such as Nitinol, or any other suitable material.

With continued reference to FIGS. 4 through 8, during assembly of the valve catheter 23, the puck 78 is snapped into the proximal end 140 of the mop 80. The slots 148 allow the proximal end 140 of the mop 80 to flex as the distal end 116 of the puck is inserted into the passageway 145 of the mop 80 (see FIGS. 7A and 8). The snap ridge 124 of the puck 78 enters the openings 146 of the mop 80, and the slot indentations 125 of the puck 78 are aligned with the areas between the openings 146 of the mop 80. The proximal end 140 of the mop 80 abuts the shoulder surface 130 of the puck 78. The collet 76 snaps into the puck 78. More particularly, the distal end 92 of the collet 76 passes through the proximal end 114 of the puck 78. The arms 104 of the collet 76 flex to pass through the central lumen 112 of the puck 78. The protrusion 138 of the puck 78 passes through one of the slots 102 of the collet 76, and is pressed tight as the slot 102 narrows. Once snapped, the flange 108 of the collet 76 bears against the distal end 116 of the puck 78, and the shoulder surface 109 of the collet 76 bears against the proximal end 114 of the puck 78.

The multi-lumen shaft 72 is placed proximally to the puck 78. The proximal end 90 of the collet 76, including the openings 96, which may be filled with an adhesive material in order to ensure a strong bond, is inserted into the central lumen 84 of the multi-lumen shaft 72 such that the side lumens 86 of the multi-lumen shaft 72 are aligned with the side lumens 136 of the puck. The connection between the multi-lumen shaft 72 and the collet 76 can be made by thermal or adhesive joining, or both. The stiffener tube 74 is placed over the multi-lumen shaft 72 near the proximal end thereof. The stiffener tube 74 extends over a portion of the multi-lumen shaft 72. The wire tube 82 is bonded to the proximal end of the multi-lumen shaft 72 and extends diagonally therefrom.

Figure 9:
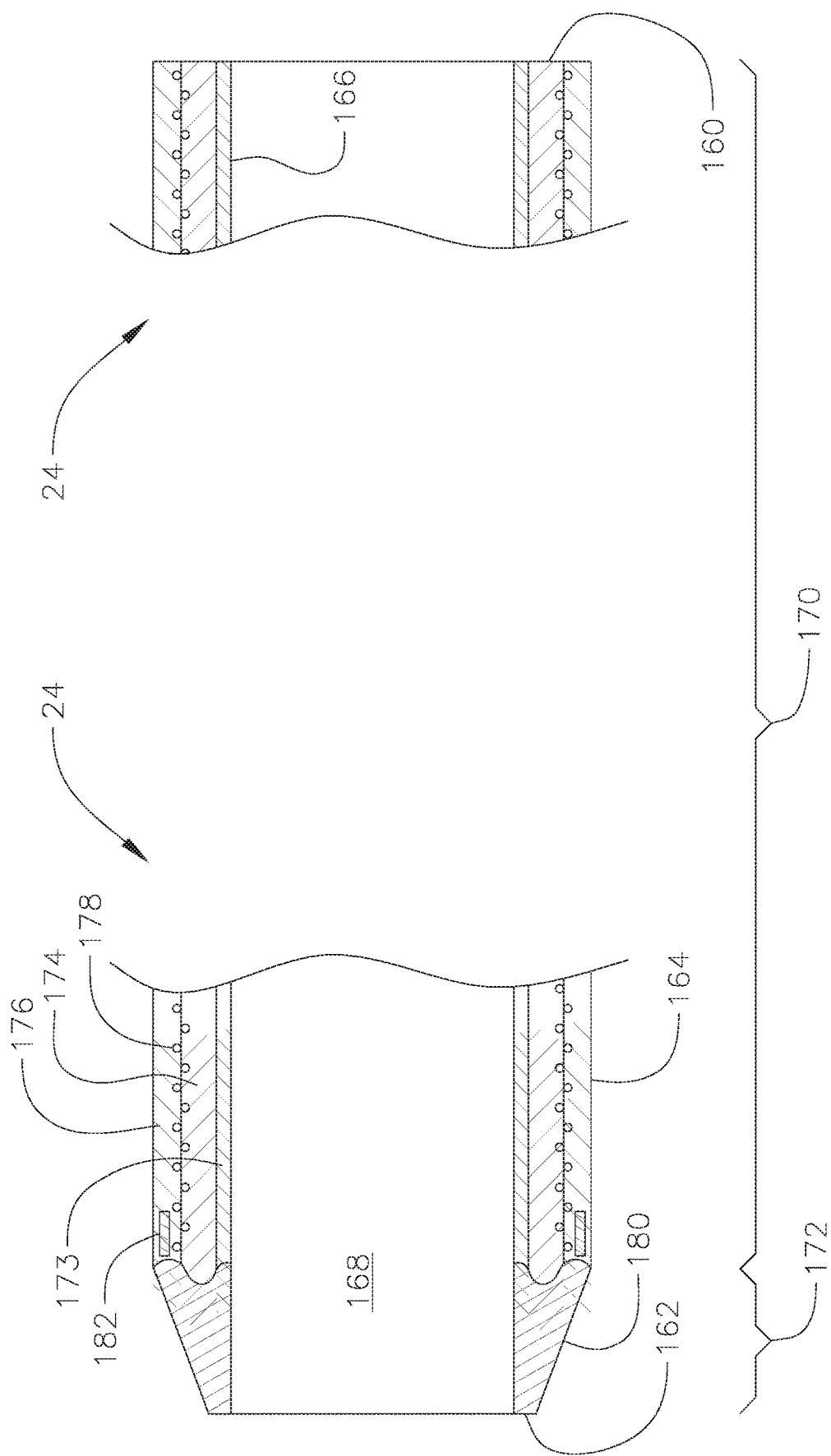
FIG. 9 is a side cross sectional view of a delivery sleeve which forms a portion of the delivery system.
Figure 10:
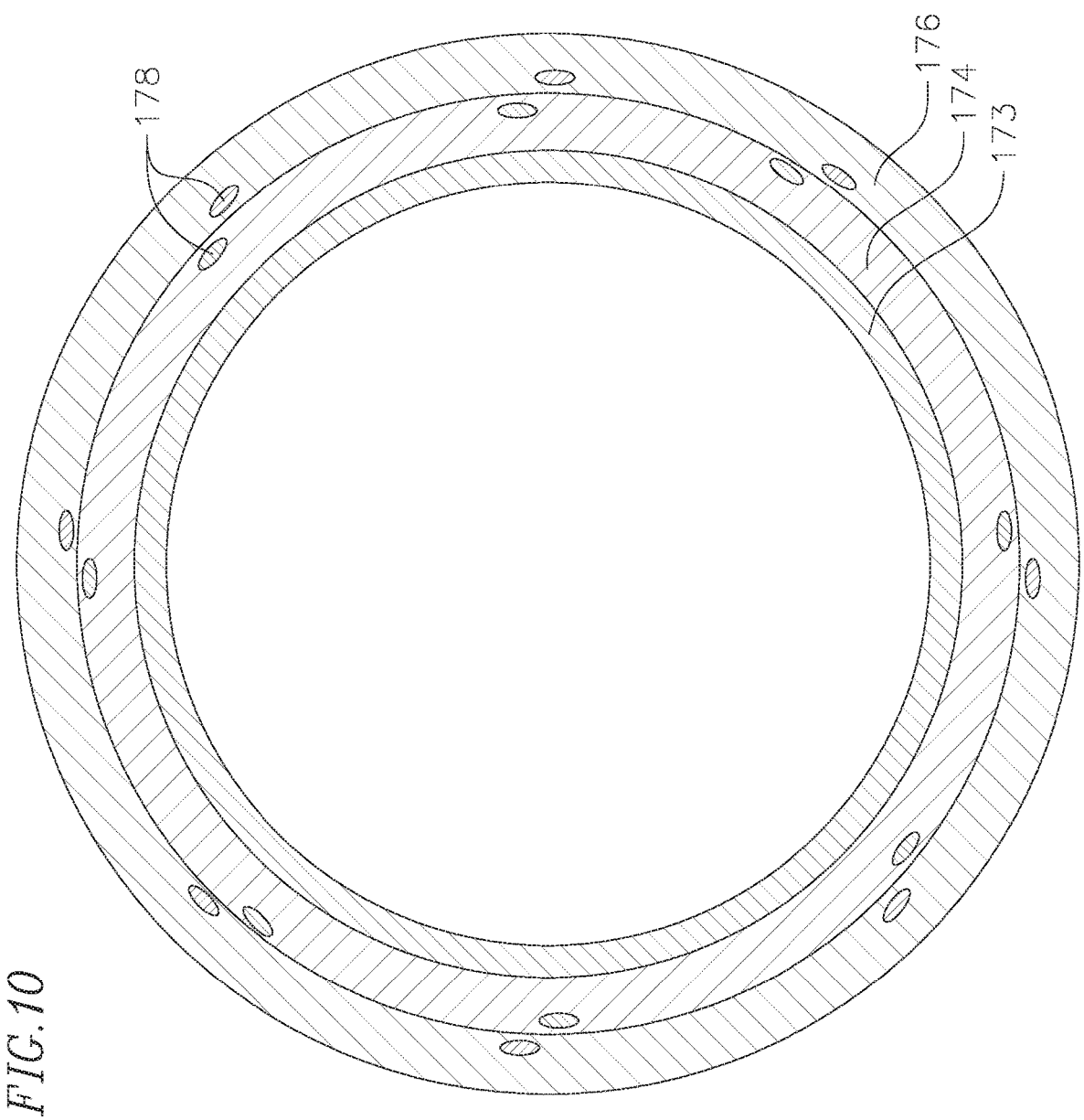
FIG. 10 is a cross sectional view along a main portion of the delivery sleeve.

With reference now to FIGS. 9 and 10, the delivery sleeve 24 preferably includes a proximal end 160, a distal end 162, an outer surface 164, an inner surface 166, and a passageway 168 extending longitudinally therethrough. The delivery sleeve 24 includes a main portion 170 and a tip portion 172. The delivery sleeve 24 contains and protects the prosthetic valve during advancement through the patient's vasculature to the native valve site, as discussed below. The main portion 170 of the delivery sleeve 24 includes an inner layer 173, over which is located a middle layer 174, over which is located an outer layer 176. The inner layer 173 of the main portion 170 of the delivery sleeve 24 is preferably formed of a material, such as Teflon®, having a low coefficient of friction. The middle and outside layers 174, 176 are preferably formed of Pebax®. At least a portion of the delivery sleeve may be coated with a lubricious material. The delivery sleeve 24 further includes a plurality of wires 178, preferably made of stainless steel, which spiral along the length of the delivery sleeve 10.

The delivery sleeve 24 is preferably formed by an extrusion process. The wires are initially placed between the middle and outer layers of the delivery sleeve 24 during the extrusion process. The delivery sleeve 24 is then laminated by heat, causing the middle and outer layers to flow. The heat of the lamination process softens the middle and outer layers 174, 176, causing the wires 178 to imbed into the middle and outer layers of the delivery sleeve 24, as shown in FIG. 10. The inner layer 173, which is preferably formed of Teflon®, does not flow when heated during the lamination process.

In one preferred construction, half of the wires 178 spiral along the length of the delivery sleeve 24 in a direction opposite that of the other half of the wires 178, such that the wires 178 cross one another to form a mesh. The wires 178 can also pass over and under one another to form a weave or a braid. The wires 178 extend from the proximal end 160 of the delivery sleeve 24 toward the distal end 162 in the main portion 170 of the delivery sleeve 24. The tip portion 172 of the delivery sleeve 10 does not contain the wires 105, which are placed in the main portion 170 of the delivery sleeve 24 to ensure adequate stiffness and pushability.

The tip portion 172 of the delivery sleeve 12 is preferably made of soft material such as Pebax®. The wires 178 and the inner layer 172 are absent at the tip portion 172 of the delivery sleeve 24. The tip portion 172 is configured such that the passageway 168 is the same size in the tip portion 172 of the delivery sleeve 24 as it is in the main portion 170 of the delivery sleeve 24. Approaching the distal end 162 of the delivery sleeve, and in the tip portion 172 of the delivery sleeve 24, the outer surface 164 tapers, forming a tapered outer surface 180, which aids in the introduction and tracking of the delivery system 10 in the body vessel, as described below.

At the transition between the main portion 170 and the tip portion 172 of the delivery sleeve, a radiopaque band 182 is disposed between the stainless steel wires 178 and outer layer 176 of the delivery sleeve 24. During the heat lamination process described above, the radiopaque band 182 does not flow. After lamination is complete, the radiopaque band 182 remains surrounding the ends of the wires 178 and thus serves as a barrier between the outer layer 176 and the wires 178. The radiopaque band 182 can comprise any suitable material, but is preferably made of an alloy comprising 90 percent platinum and 10 percent iridium (PLIR).

Figure 11:
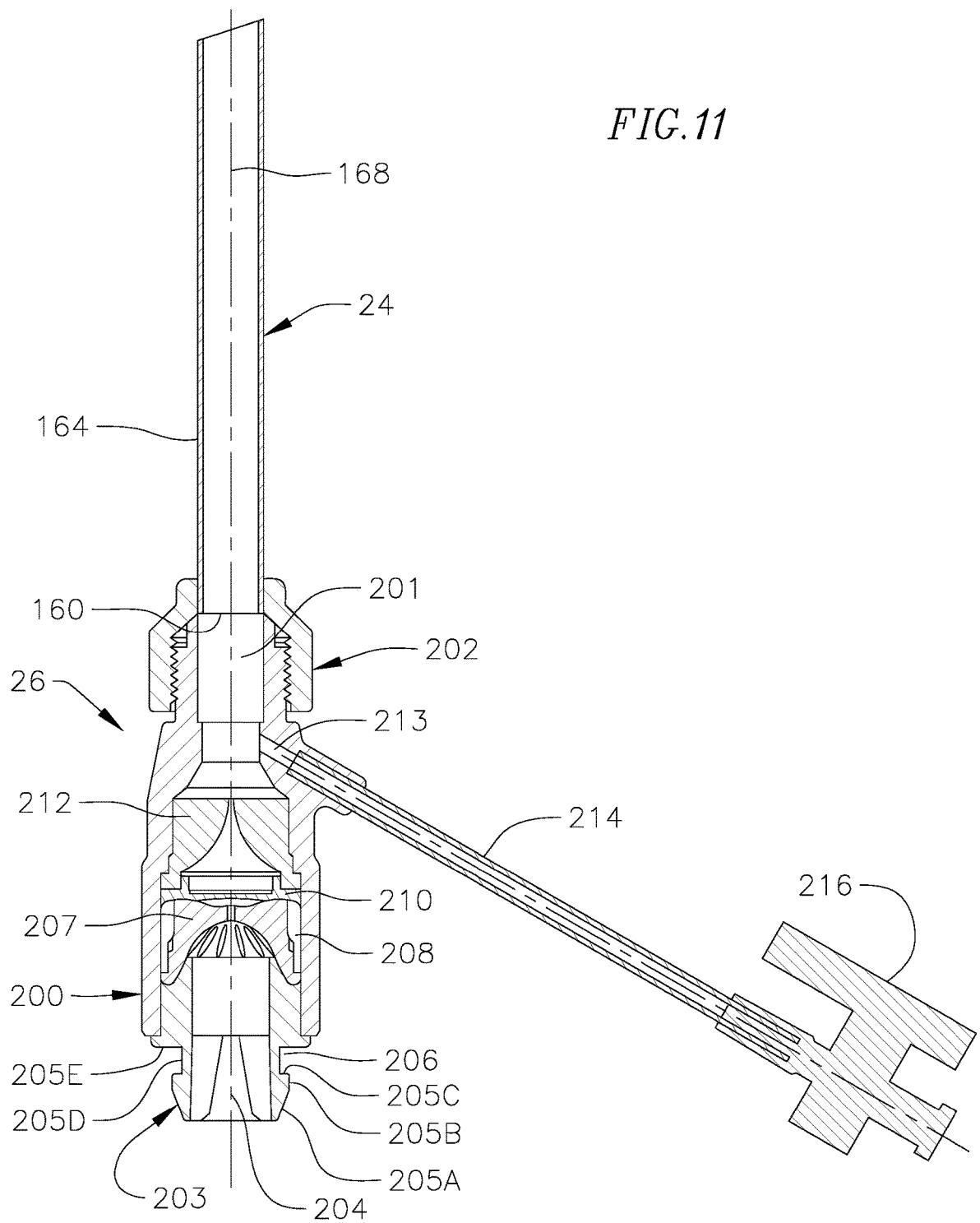
FIG. 11 is a side cross sectional view of a proximal hub of the delivery system.

With reference now to FIG. 11, a cross-sectional view along the proximal hub 26 of the delivery sleeve 24 is provided. The proximal hub 26 preferably comprises a cylindrically shaped hub body 200 having a passageway 201 extending longitudinally therethrough. The hub body 200 is partially surrounded by a housing 202 located at a distal end of the hub body 200. An end piece 203 having an opening 204 extending into the passageway 201 of the hub body 200 is mounted to a proximal end of the hub body 200 and protrudes therefrom. An outer surface of the end piece 203 includes, when viewed from a proximal end to a distal end, a tapered surface 205A, a first neck surface 205B, a first shoulder surface 205C facing distally, a second neck surface 205D, and a second shoulder surface 205E facing proximally. The first shoulder surface 205C, the second neck surface 205D, and the second shoulder surface 205E define a groove 206 extending around the end piece 203.

Proximally adjacent the end piece 203 and inside the hub body 200, a cross cut valve 207 is located, and is partially surrounded by a spacer 208. Proximally adjacent the cross cut valve 206 and spacer 208 and inside the hub body 200, a disc valve 210 is located. A duck bill valve 212 is also located inside the hub body 200, proximally adjacent to the disc valve 210. A hemostasis opening 212 extends from the passageway 201, and a hemostasis tube 214 extends from the hub body 200 to a three-way stopcock 216. One preferred embodiment of the proximal hub is described in greater detail in U.S. Pat. No. 5,968,068 entitled ENDOVASCULAR DELIVERY SYSTEM, the contents of which are fully incorporated herein by reference.

With continued reference to FIG. 11, the delivery sleeve 24 is secured to the proximal hub 26. The proximal end 160 of the delivery sleeve 24 is inserted into the passageway 201 of the proximal hub 26 at a distal end thereof. The outer surface 164 of the delivery sleeve 24 is secured to an inner surface of the housing 202 of the proximal hub 26 by an adhesive or thermal joining, thus placing the passageway 201 of the proximal hub in communication with the passageway 168 of the delivery sleeve 24.

With reference now to FIG. 12 through 15, one preferred embodiment of the handle assembly 500 will be described. The illustrated handle assembly 500 provides a mechanical actuation mechanism for advancing the prosthetic valve from the distal end of the delivery sleeve 24 in a controlled and precise manner. The handle assembly 500 includes, generally, a distal plate assembly 502 coupled to the proximal hub 26 on the proximal end of the delivery sleeve 24. The handle assembly also includes a proximal plate assembly 504 coupled to the valve catheter 23. A lead screw 506 passes through the distal and proximal plate assemblies 502, 504.

Figure 13A:
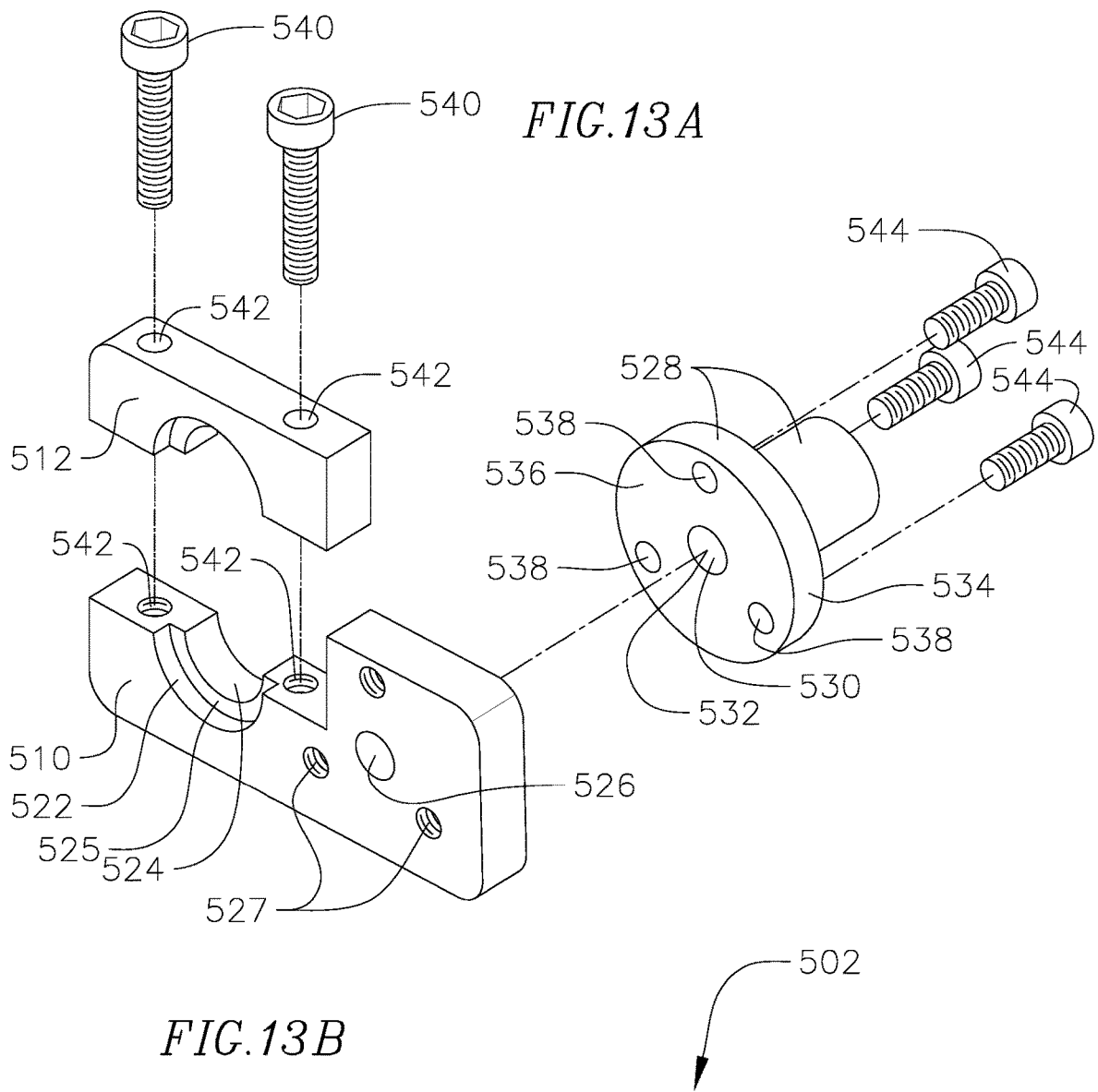
FIGS. 13A and 13B are exploded and perspective views, respectively, of a distal plate assembly of the handle assembly.
Figure 13B:
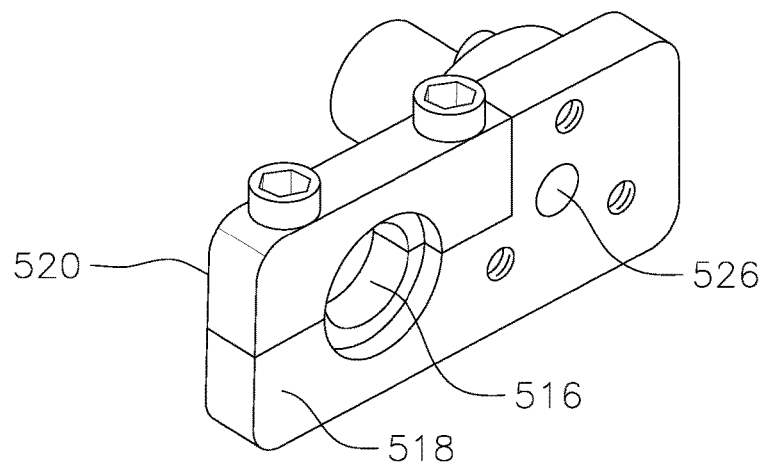

With particular reference to FIGS. 13A and 13B, the distal plate assembly 502 includes a main portion 510, an upper portion 512, and a lead screw nut 514. The main and upper portions 510, 512 combine to include a first opening 516 passing through from a proximal face 518 to a distal face 520 of the distal plate assembly 502. The first opening 516 is defined by a proximal opening surface 522, a distal opening surface 524, and a shoulder surface 525. The proximal and distal opening surfaces 522, 524 extend perpendicularly from the proximal and distal faces 518, 520 of the distal plate assembly 502. The shoulder surface 525 faces proximally and extends between the proximal and distal opening surfaces 522, 524, substantially parallel to the proximal and distal faces 518, 520 of the distal plate assembly 502. A second opening 526 in the distal plate assembly 502 extends from the proximal face 518 to the distal face 520. Fastener openings 527 likewise extending through the distal plate assembly 502 are located in the area of the second opening 526.

The lead screw nut 514 is tube shaped, having an outer surface 528, an inner surface 530, and an opening 532 extending longitudinally therethrough. An outwardly extending flange 534 extends outwardly adjacent a proximal end 536 of the lead screw nut 514. Fastener openings 538 pass through the flange 534 to the proximal end 536 of the lead screw nut 514. The inner surface 530 of the lead screw nut 514 is threaded.

The upper portion 512 of the distal plate assembly 502 is secured to the main portion 510 of the distal plate assembly 502 by distal plate assembly fasteners 540, which engage distal plate assembly fastener holes 542. The distal plate assembly fastener holes 542 pass through the upper portion 512 of the distal plate assembly 502 and into the main portion 510 of the distal plate assembly 502.

The lead screw nut 514 is secured to the main portion 510 of the distal plate assembly 502 as the proximal end 536 of the lead screw nut 514 is placed against the distal face 520 of the main portion 510, and fastener openings 527 of the main portion 510 are aligned with the fastener openings 538 of the lead screw nut 514. The opening 532 in the lead screw nut 514 is aligned with the second opening 526 of the distal plate assembly 502. Lead screw nut fasteners 544 engage the fastener openings 527, 538 and secure the lead screw nut 514 to the main portion 510 of the distal plate assembly 502.

Figure 14A:
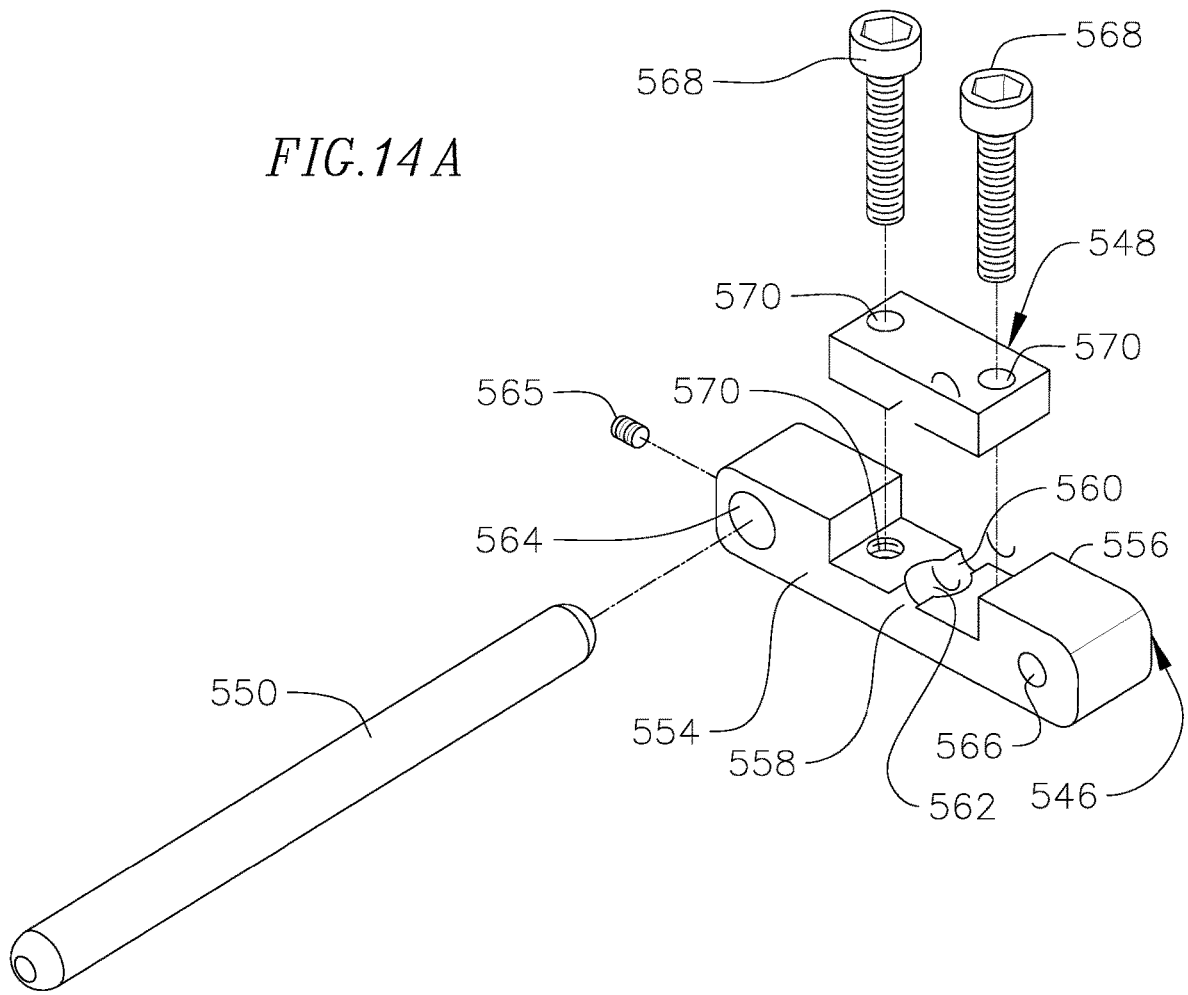
FIGS. 14A and 14B are exploded and perspective views, respectively, of a proximal plate assembly of the handle assembly.
Figure 14B:
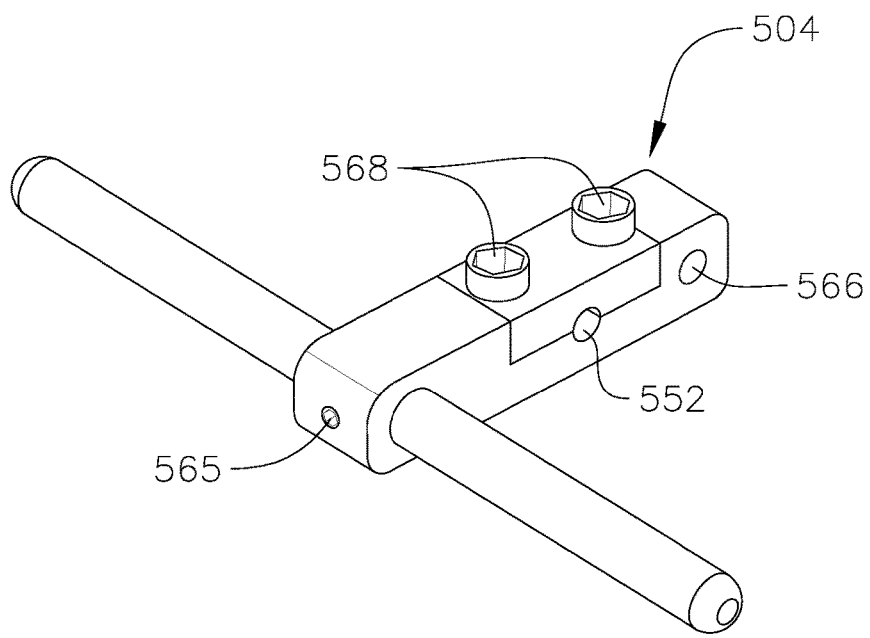

With reference to FIGS. 14A and 14B, the proximal plate assembly 504 includes a main portion 546, a cap portion 548, and a handle 550 extending from the main portion 546. The main portion 546 and cap portion 548 combine to create a central opening 552 passing through from a proximal face 554 to a distal face 556. The central opening 552 is defined by a proximal opening surface 558, a distal opening surface 560, and an inner cavity surface 562. The proximal and distal opening surfaces 558, 560 extend perpendicularly from the proximal and distal faces 554, 556 of the proximal plate assembly 504. The inner cavity surface 562 runs between the proximal and distal opening surfaces 558, 560, and creates an open cavity within the assembled proximal plate assembly 504.

A first side opening 564 in the proximal plate assembly 504 extends from the proximal face 554 to the distal face 556. The handle 550 is secured to the main portion 546 of the proximal plate assembly 504 such that it passes through the first side opening 564 and is secured by a set screw 565. A second side opening 566 in the proximal plate assembly 504 also extends from the proximal face 554 to the distal face 556. The cap portion 548 of the proximal plate assembly 504 is secured to the main portion 546 of the proximal plate assembly 504 by proximal plate assembly fasteners 568, which engage proximal plate assembly fastener holes 570. The proximal plate assembly fastener holes 570 pass through the cap portion 548 of the proximal plate assembly 504 and into the main portion 546 of the proximal plate assembly 504.

With reference to FIG. 15, the lead screw 506 includes a rotator knob 572 at a proximal end thereof, a non-threaded portion 574, and a threaded portion 576 adjacent a distal end thereof. The rotator knob 572 includes a neck portion 578 extending distally therefrom and from which the non-threaded portion 574 extends distally. A shoulder surface 580 at a distal end of the neck portion 578 of the rotator knob 572 faces distally. A groove 581 extends circumferentially around the lead screw 506.

With reference again to FIGS. 12 through 15, the handle assembly 500 is assembled as the lead screw 506 is placed through the second side opening 566 and lead screw nut opening 532 of the proximal plate assembly 504 and the second opening 526 of the distal plate assembly 502 such that the shoulder surface 580 of the rotator knob 572 abuts the proximal face 554 of the proximal plate assembly 504. A snap ring 582 is placed in the groove 581 on the non-threaded portion 574 of the lead screw 506 such that it abuts the distal face 556 of the proximal plate assembly 504. The snap ring 582 on the distal face 556 and the shoulder surface 580 on the proximal face 554 prevent translational movement of the lead screw 514 through the second side opening 556 of the proximal plate assembly 504. The lead screw 506 rotates in the second side opening 556 of the proximal plate assembly 504. The threaded portion 576 of the lead screw 506 engages the threaded inner surface 530 of the lead screw nut 514.

With reference to FIG. 16, an alternative embodiment of the handle assembly 500 is shown wherein the lead screw nut 514 is located proximally from the distal plate assembly 502. A middle plate 590 surrounds the lead screw nut 514, and lead screw nut fasteners 544 secure the middle plate 590 to the lead screw nut 514. The middle plate 590 is secured to a load cell 592, which is secured to the distal plate assembly 502. The load cell 592 as shown in FIG. 16 is known in the art, and may be connected as known in the art to a device (not shown) which measures the displacement on the load cell 592. The device converts the displacement of the load cell 592 to the force being exerted to move the distal plate assembly 502 relative to the middle plate 590.

With reference to FIG. 17, another alternative embodiment of the handle assembly 500 includes a forked portion 594 of the middle plate 590 extending toward the handle 550, which passes through an opening 596 of the forked portion 594. A second handle 598 passes through the distal plate assembly 502, and is secured by a second set screw 600, which passes through the distal plate assembly 502 to contact the second handle 598. A handle opening 602 in the distal assembly plate 502 allows the handle 550, secured to the proximal plate assembly 504, to pass through the distal plate assembly 502 unimpeded.

Figure 18:
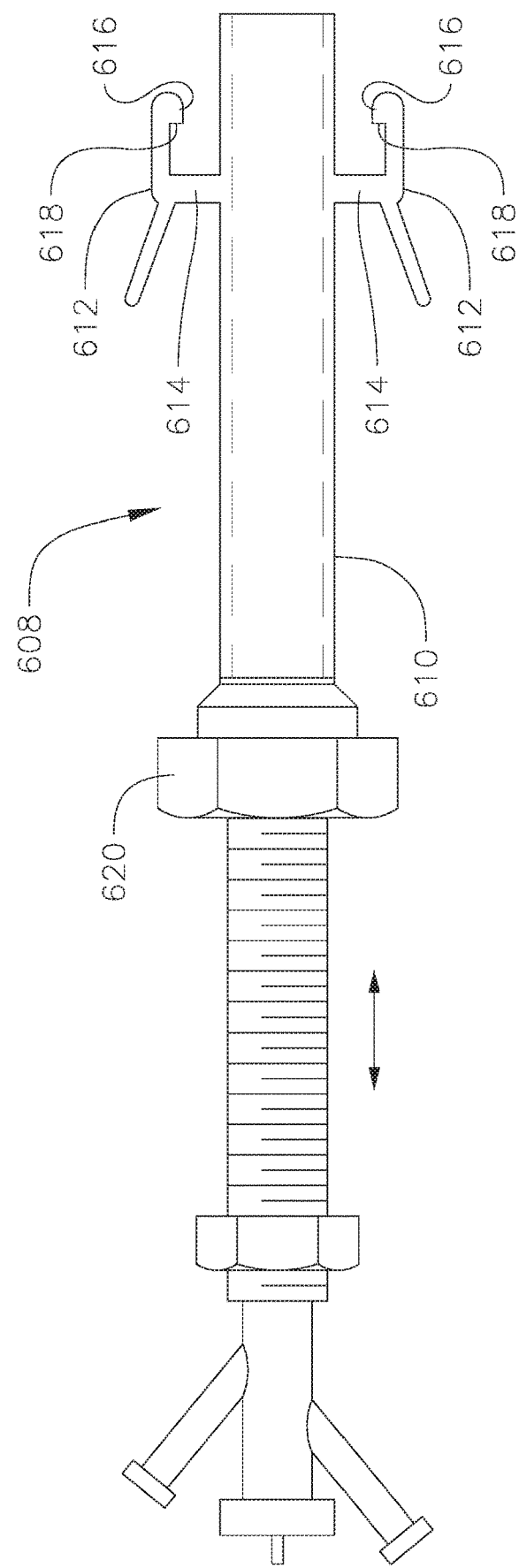
FIG. 18 is a side view of yet another embodiment of a handle assembly.

With reference to FIG. 18, another alternative handle assembly 608 is illustrated wherein the proximal and distal plate assemblies are not required. A hollow shaft 610 includes snap members 612 extending parallel thereto. The snap members 612 are connected to the shaft 610 by bridges 614 extending between the shaft 610 and the snap members 612. At a distal end, the snap members 612 include flanges 616 extending inwardly toward the shaft 610, forming proximally facing surfaces 618. A deployment knob 620 having an inner threaded surface is rotatably coupled to the shaft 610.

Figure 19:
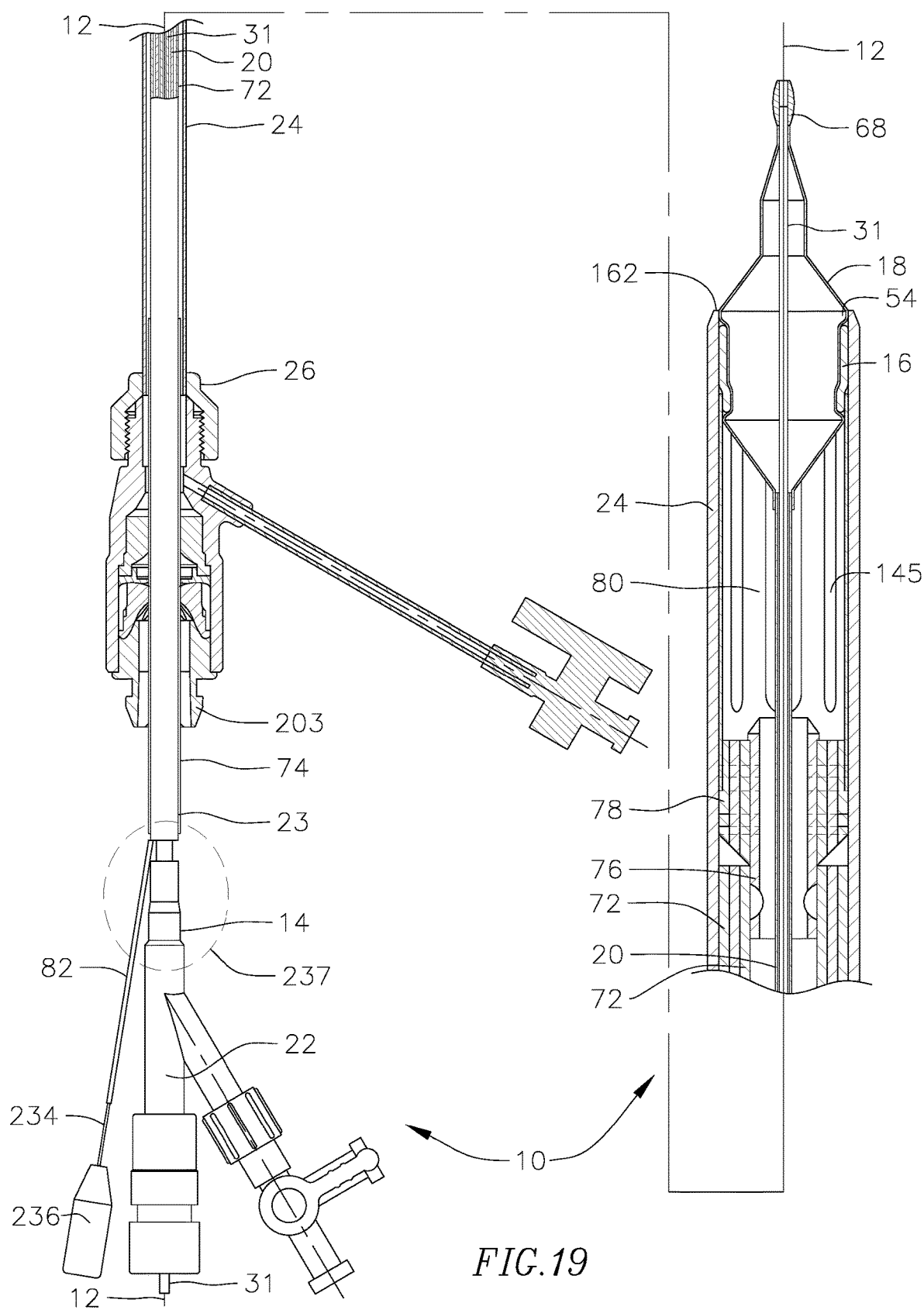
FIG. 19 is a side view of the delivery system, with the proximal hub and distal end portion of the delivery system shown in cross section.

With reference now to FIG. 19, the functionality of the delivery system 10 will be described in more detail. The balloon catheter 14 is configured for insertion into the valve catheter 23. The balloon shaft 20 is placed in the central lumen 84 of the multi-lumen shaft 72 and the outer surface 38 of the balloon shaft 20 is secured to an inner surface of the multi-lumen shaft 72, such as, for example, by adhesion.

The balloon shaft 20 extends from the support 22, located proximal to the proximal end of the multi-lumen shaft 72, through the central lumen 84 of the multi-lumen shaft 72, through the passageway 94 of the collet 76, through the central lumen 112 of the puck 78, to the passageway 145 of the mop 80. The main cylindrical portion 54 of the balloon 18 extends distally from the distal end 156 of the mop 80. The prosthetic valve 16 is crimped sufficiently small to enter into the passageway 168 of the delivery sleeve 24. The prosthetic valve 16 is supported by the main cylindrical portion 54 of the balloon 18 and is placed against the inner surface 166 of the delivery sleeve 24 in the area of the tip portion 172, where it is contained while tracking to the native valve site.

The delivery system 10 is preferably configured for use with a self-expanding prosthetic valve 16. In one preferred embodiment, the prosthetic valve is formed, at least in part, of a memory material, such as Nitinol, wherein the prosthetic valve takes a rigid shape at a predetermined temperature, but is more malleable at lower temperatures. An example of such a self-expanding prosthetic valve is described in more detail in U.S. Patent Publication No. 2004/0186563 A1, published Sep. 23, 2004, the contents of which are fully incorporated herein by reference. It will be appreciated however, that many features of the present invention may also be used with other types of prosthetic valves, such as, for example, balloon expandable valves. Examples of preferred balloon expandable prosthetic valves are disclosed in U.S. Pat. No. 6,730,118 entitled IMPLANTABLE PROSTHETIC VALVE and U.S. Pat. No. 6,893,460, also entitled IMPLANTABLE PROSTHETIC VALVE, both of which are fully incorporated herein by reference.

With continued reference to FIG. 19, the delivery sleeve 24 and proximal hub 26 are placed over the valve catheter 23. The valve catheter 23 passes through the opening 204 of the end piece 203, the passageway 201 of the proximal hub 26 (including valves 207, 210, and 212), and the passageway 168 of the delivery sleeve 24 (see FIG. 11). The proximal hub 26 is located near the proximal end of the valve catheter 23, with the stiffener tube 74 entering the passageway 201 of the proximal hub 26 (see FIG. 11) and extending proximally therefrom. The prosthetic valve 16 is located in the passageway 168 near the distal end 162 of the delivery sleeve 24 (see FIG. 11). The self-expanding prosthetic valve 16 can be crimped to fit inside a delivery device when subject to temperatures lower than body temperature. The balloon 18 protrudes distally from the distal end 162 of the delivery sleeve 24.

The guide wire 12 is inserted into the passageway 71 of the guidewire shaft 31. The guide wire 12 extends distally from the distal end of the guidewire shaft 31 and from the soft tip 68, and proximally from a proximal end of the guidewire shaft 31.

A bonded wire 234 extends through the wire tube 82. The bonded wire forms a portion of a preferred actuation mechanism for releasing the prosthetic valve from the valve catheter at the treatment site. The bonded wire 234 is formed from six individual wires which exit the wire tube 82 at a distal end thereof and enter the six side lumens 86 of the multi-lumen shaft 72. A knob 236 sits on a proximal end of the bonded wire 234. The six individual wires of the bonded wire 234 exit the distal end of the multi-lumen shaft and enter the side lumens 136 of the puck 78 (see FIGS. 7A and 7B). The six individual wires of the bonded wire 234 exit the side lumens 136 at the distal end 116 of the puck 78 and extend toward the distal end 156 of the mop 80.

Heat shrink 237 can be used to reinforce the connection between the multi-lumen shaft 72, the wire tube 82, and the balloon catheter 14. The heat shrink 237 is placed over the wire tube 82, the multi-lumen shaft 72, and the main shaft 32 of the support 22, and is heat treated until it forms a hardened shell around the components, thus securing them to one another and making the delivery system 10 more robust.

Figure 20:
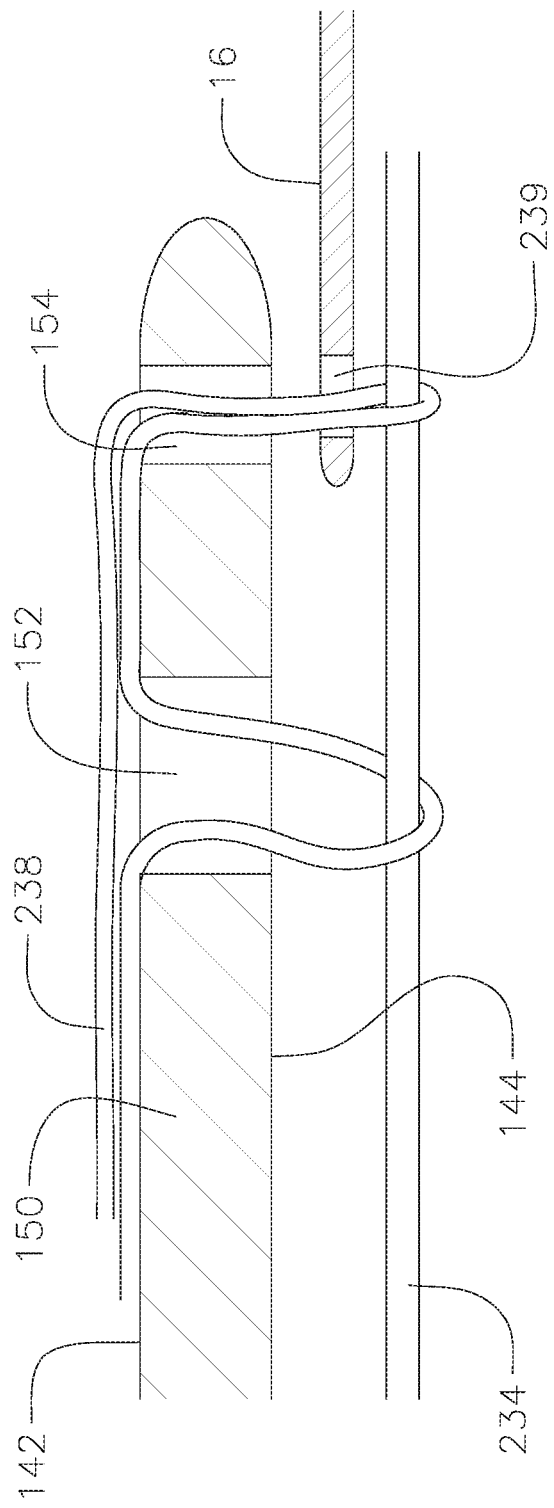
FIG. 20 is a cross sectional view of an extension of the mop and corresponding prosthetic valve portion.

With reference now to FIG. 20, one preferred means for releasably attaching the prosthetic valve 16 to the valve catheter will be described. In general terms, the prosthetic valve 16 is preferably attached to the mop 80 portion of the valve catheter (see FIG. 8) by a flexible elongate member to provide a tether and snare mechanism. To accomplish this, one or more sutures 238 (tethers) are passed through portions of the prosthetic valve and through the mop 80 portion of the valve catheter. The sutures 238 preferably include loops that extend through portions of the prosthetic valve. Slidable wire(s) 234 extend through the loops to prevent the suture from detaching from the prosthetic valve. Therefore, the slidable wire(s) 234 provide a releasable snare mechanism that can be withdrawn for quickly and easily detaching the sutures from the prosthetic valve.

In the preferred embodiment illustrated in FIG. 20, proximal end portions of the prosthetic valve 16 are placed near the second openings 154 on the inner surface 144 of the mop 80. The six individual wires of the wire 234 extend from the side lumens 136 of the puck 78 (see FIG. 7A) and are pressed against the inner surface 144 of the extensions 150 of the mop 80. The individual wires pass along the sides of the prosthetic valve 16, with the prosthetic valve 16 placed between the inner surface 144 of the mop 80 and the individual wires. Distal ends of the individual wires can be tucked into a commissure pocket of the prosthetic valve 16 or between leaflets at a commissure post of the prosthetic valve 16 to avoid exposure to the delivery sleeve 24 while tracking and to the body vessel during valve deployment.

An anchor, such as a ring formed of suture or other material, is preferably provided in the annular groove 123 of the puck 78 (see FIG. 7A). The suture 238 is tied into the anchor, and then passes therefrom along the outer surface 142 of the mop 80 (see also FIG. 8), whereupon it passes through the first opening 152 of one of the extensions 150 of the mop 80, wraps around the individual wire of the wire 234, and returns to the outer surface 142 of the mop 80 through the first opening 152. The suture 238 then passes through the second opening 154 of one of the extensions 150 of the mop 80, through an attachment opening 239 of the prosthetic valve 16, around the individual wire 234, returns through the attachment point of the prosthetic valve 16, and returns through the second opening 154 of the same extension 150 to the outer surface 142 of the mop 80. The suture 238 is tied into the anchor at the annular groove 123 of the puck 78 such that it forms a suture loop extending from the anchor to the distal end 156 of the extension 150 of the mop 80 (see also FIG. 8). The suture 238 is used to form a similar suture loop corresponding to each extension 150 of the mop 80, with a tether or snare formed near the distal end 156 of each extension 150 of the mop 80. The suture 238 is wrapped around itself and tied into a position aligned with each extension 150 of the mop before passing along the outer surface 142 of each extension 150 to form the suture loop.

With reference again to FIGS. 12 through 18, attachment of the handle assembly 500 to the delivery system 10 will now be described in more detail. The proximal plate assembly 504 clenches the valve catheter 23, which is inserted into the central opening 552 of the proximal plate assembly 504. The stiffener tube 74 (see FIG. 4) of the valve catheter 23 contacts the proximal and distal opening surfaces 558, 560 of the proximal plate assembly 504 (see FIG. 14A). The contact is sufficiently tight to secure the valve catheter 23 to the proximal plate assembly 504.

The distal plate assembly 502 is secured to the proximal hub 26. The end piece 203 passes through the first opening 516 of the distal plate assembly 502 (see FIG. 13B), with the distal plate assembly 502 engaging the groove 506 of the end piece 203 (see FIG. 11). The first neck surface 205B of the end piece 203 (see FIG. 11) bears against the proximal opening surface 522 of the distal plate assembly 502 (see FIGS. 13A and 13B). The first shoulder surface 205C of the end piece 203 (see FIG. 11) bears against the shoulder surface 525 of the distal plate assembly 502 (see FIGS. 13A and 13B). The second neck surface 205D of the end piece 203 (see FIG. 11) bears against the distal opening surface 524 of the distal plate assembly 502 (see FIGS. 13A and 13B). The second shoulder surface 205E of the end piece 203 (see FIG. 11) bears against the distal face 520 of the distal plate assembly 502 (see FIGS. 13A and 13B).

The embodiments shown in FIGS. 16 and 17 are well-suited for allowing the operator to be aware of the force being exerted on the prosthetic valve 16 while it is exiting the delivery sleeve 24, described below. The embodiment shown in FIG. 17 is suited to stabilize the handle assembly 500, as the extended distal plate assembly 502 and second handle 598 cause an even distribution of weight about an axis defined by the valve catheter 23. The forked portion 594, in addition to serving as a means to evenly distribute weight about the axis defined by the valve catheter 23, serves to prevent the device from rotating under the stresses present during valve deployment and operation of the lead screw 506, described below.

Figure 21:
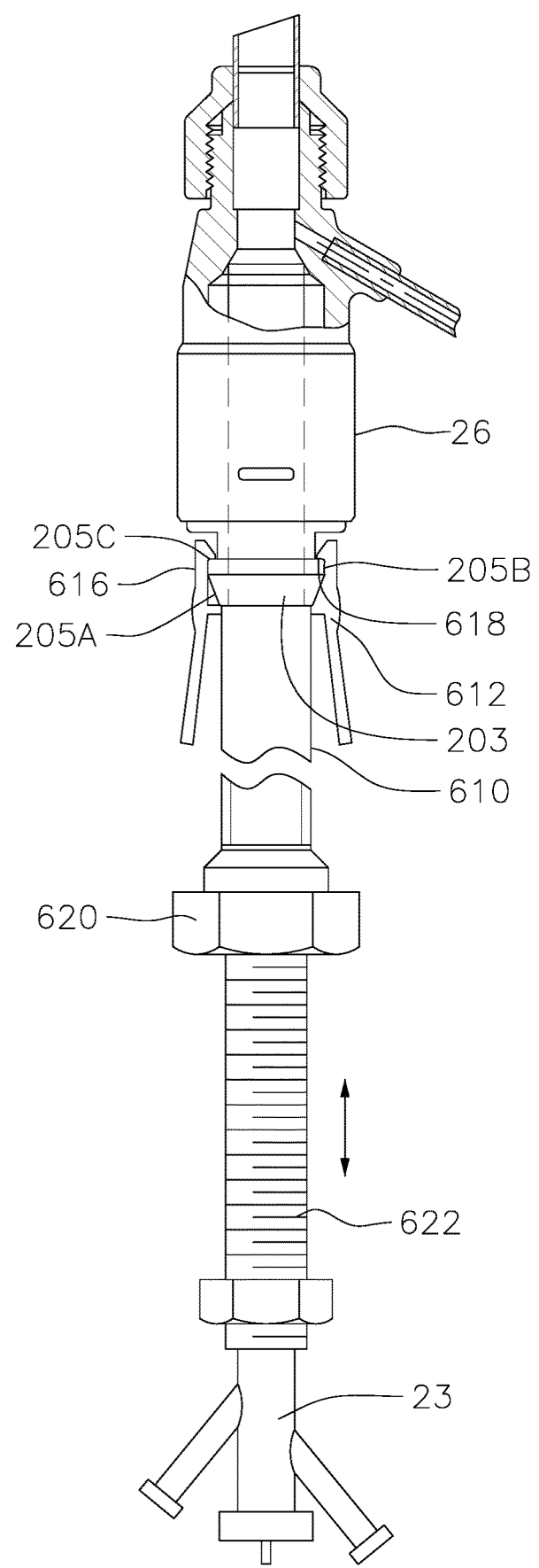
FIG. 21 is a side view of the assembly between the alternative handle assembly of FIG. 18 and the delivery system.

In the alternative embodiment shown in FIG. 18, the handle assembly 608 is attached to the delivery system 10 by snapping the shaft 610 into the proximal hub 26 (see FIG. 11), as shown in FIG. 21. The shaft 610 enters the opening 204 of the end piece 203 (see FIG. 11). The flanges 616 of the snap members 612 pass over the tapered surface 205A and the first neck surface 205B to engage the groove 206 (see FIG. 11) of the end piece 203. The proximally facing surfaces 618 of the snap members 612 bear against the first shoulder surface 205C of the end piece 203 of the proximal hub 26. The inner threaded surface of the deployment knob engages a threaded surface 622 of the valve catheter 23. The threaded surface 622 of the valve catheter 23 can be incorporated into the stiffener tube 74 (see FIG. 4)

With reference now to FIGS. 1 through 11, preferred methods of using the delivery system 10 to deliver a prosthetic valve 16 will be described in more detail. The guide wire 12 is first inserted into a body vessel, such as the femoral artery, according to methods that are known in the art. The guide wire 12 passes through the arteries of the patient, and through an opening in the native valve. If desired, a dilator may be inserted over the guide wire 12 into the body cavity. One preferred dilator is described in more detail in U.S. Pat. No. 5,968,068 entitled ENDOVASCULAR DELIVERY SYSTEM, the contents of which are fully incorporated herein by reference. The dilator acts to enlarge the opening of the body vessel and thereby facilitate the passing of the delivery system 10 into the body vessel. After vessel dilation and entry of the delivery system 10 into the body vessel, the dilator is removed. However, as discussed above, embodiments of the delivery system 10 may be used without a dilator due to the shape and coating of the balloon and delivery sleeve.

The delivery system 10 travels over the guide wire 12 and is introduced into the body vessel. A hydrophilic coating is preferably used to provide lubricity on the outer surface 46 of the balloon 18 (see FIG. 3A) and on the outer surface 164 of the delivery sleeve 24 (see FIG. 11). A lubricious surface allows for easier introduction of the device, as well as easier tracking of the device to the site of the native valve, by decreasing the amount of friction between the walls of the body vessel through which the device is tracked. The outer surface 46 of the second cone portion 56 of the balloon 18 (see FIGS. 3A and 3B) provides a tapered surface for ease of entry into the body vessel. At the distal end 162 of the delivery sleeve 24, the tapered surface 180 of the tip portion 172 of the delivery sleeve 24 (see FIG. 9) also facilitates entry into the body vessel.

Figure 22A:
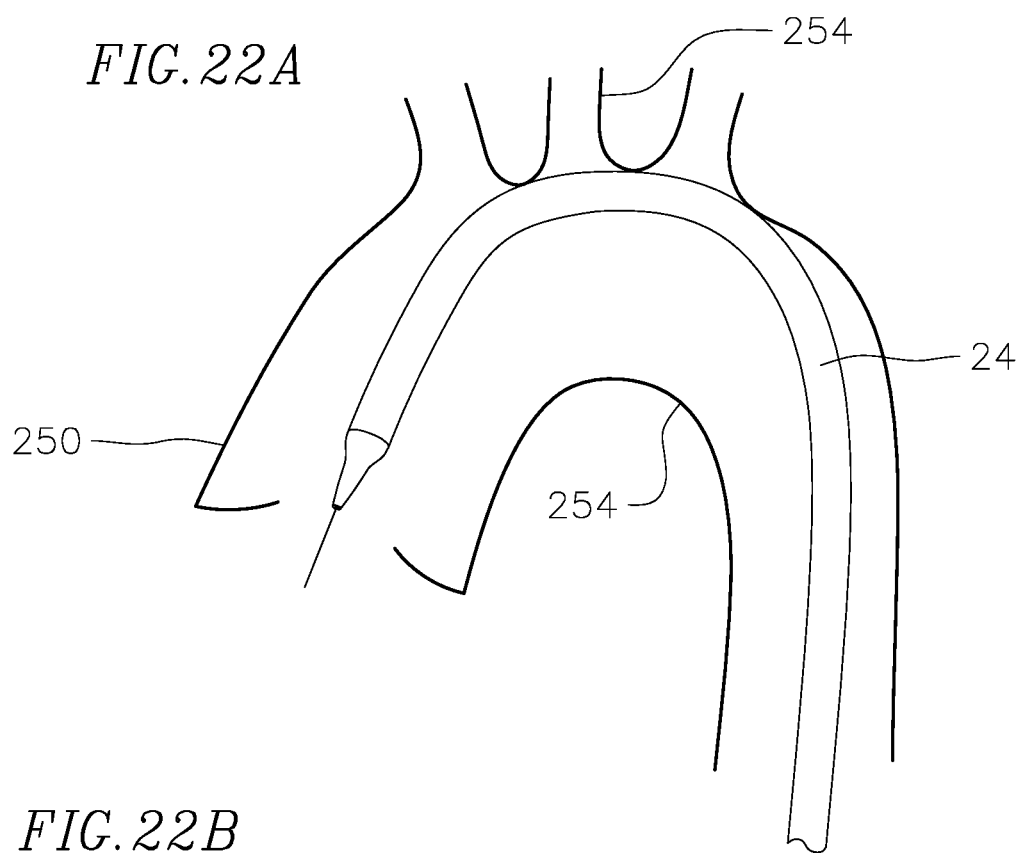
FIGS. 22A and 22B show the delivery system approaching a native valve site, and pushing away diseased native valve leaflets, respectively.

With reference now to FIG. 22A, the delivery system 10 passes over the guide wire 12 as it tracks to a native valve site 250. Tracking occurs as the operator pushes the delivery system 10 through the femoral artery, over the aortic arch 254, and to the native valve site 250 in a retrograde (i.e., against the blood flow) procedure. The balloon 18 may be used to act as a dilator within the body vessel during tracking. The body vessel may be constrictive due to size or calcification. The balloon 18 provides a tapered, soft surface, for gradual dilation of constrictive areas of the body vessel as the distal end of the delivery system 10 advances therethrough. If necessary, the balloon may be partially or entirely deflated and then re-inflated during advancement to further facilitate advancement through narrow vasculature. The structure of the delivery sleeve 24 gives it sufficient flexibility and pushability to track to the native valve site 250. Fluoroscopy, wherein the position of the radiopaque band 182 of the delivery sleeve 24 (see FIG. 9) can be seen relative the native valve site 250, allows the operator to be aware of the position of the delivery system 10.

During tracking of the delivery system 10 to the native valve site, the delivery sleeve 24 bends in order to pass through the curves of the body vessels, including the curve found in the aortic arch 254. The bending of the delivery sleeve 24 may cause the components of the valve catheter 23 to move relative to the inner surface 166 of the delivery sleeve 24 (see FIG. 9). The bending may also cause the passageway of the delivery sleeve 24 to narrow, thereby increasing friction. Accordingly, preferred embodiments of the delivery sleeve 24 have an inner surface 166 formed or coated with a material having a low coefficient of friction such as Teflon®.

As the delivery sleeve 24 bends while tracking to the native valve site 250, a bending force is exerted on the wires 178 (see FIG. 10). The force on the wires 178 may cause the wires 178 to press against the middle and outer layers 174 and 176 of the delivery sleeve 24. Accordingly, the radiopaque band 182 (see FIG. 9) is preferably formed from material that is sufficiently puncture resistant such that forces exerted by the ends of the wires 178 cannot puncture the outer layer 176 of the delivery sleeve 24 when the sleeve 24 is bending. The inner layer 173 of the delivery sleeve 24 (see FIG. 10) also provides protection to the valve catheter 23 and balloon catheter 14 from the wires 178. The material chosen for the inner layer 173 does not flow under the heat laminating process described above. The wires 178 do not become imbedded in the inner layer 173. The inner layer 173 thus provides a barrier between the wires 178 and the passageway 168 of the delivery sleeve 24.

Figure 22B:
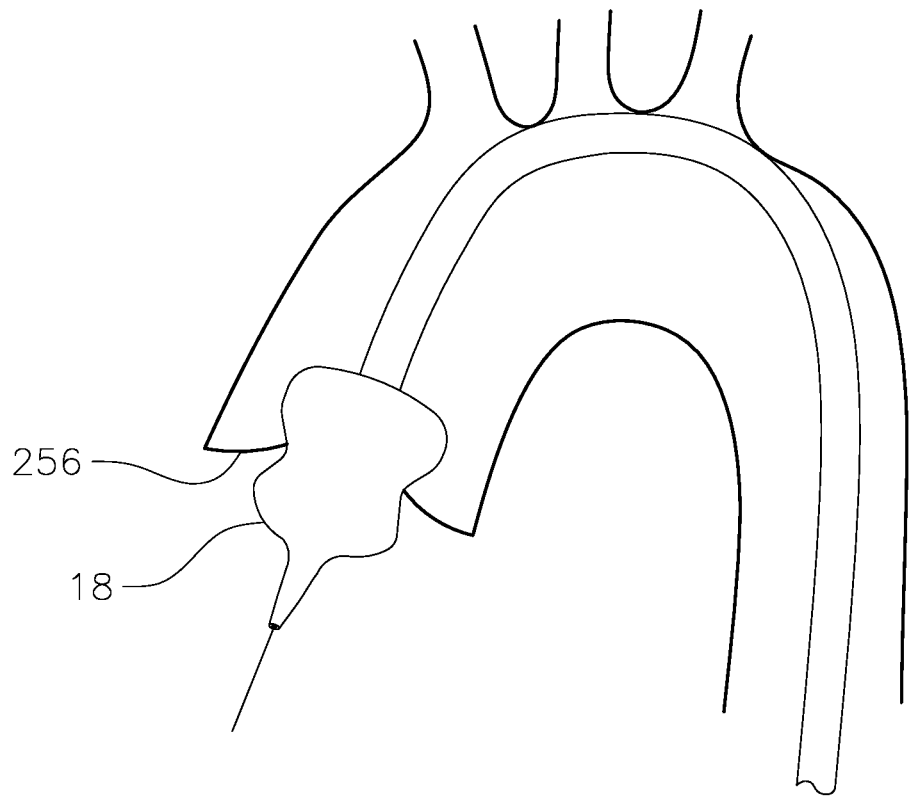

With reference to FIG. 22B, once the delivery system 10 has arrived at the valve site, the operator can push the prosthetic valve 16 (see FIG. 1) across native valve leaflets 256, thus loosening the leaflets 256 that have become stenotic. Aortic stenosis is a disease of the aortic valve of the heart. Stenotic leaflets are thickened, hardened, and calcified; their movement is more limited than healthy leaflets. Stenotic leaflets inhibit blood flow, leaving only a small hole from which blood can be ejected into the aorta. Valve implantation can require that the leaflets be removed or pushed out of the way. However, the hardened nature of stenotic leaflets can complicate the loosening process.

The balloon 18 is capable of stiffening when inflated and can be used to dilate stenotic leaflets of a native heart valve. The balloon 18 is deflated and the second cone portion 56 of the balloon 18 is passed through a small opening between the stenotic leaflets. The balloon 18 is then reinflated, as shown in FIG. 22B, and the expanding balloon exerts sufficient pressure on the hardened tissue of the stenotic leaflets to dilate the leaflets. This dilation aids in the deployment of the prosthetic valve 16 (see FIG. 19), described below.

In a preferred method of valve deployment, the delivery sleeve 24 retracts as the valve catheter 23 is held steady, exposing the prosthetic valve 16 to an implantation site without requiring that the prosthetic valve track through the body cavity while exposed thereto. Further, there is no need to track the valve through a guide or introducer sheath, as it remains stationary with respect to the delivery sleeve 24 during introduction into the body vessel and during tracking therethrough.

In the embodiment shown in FIGS. 12, 16, and 17, wherein the handle assembly 500 is employed, the operator turns the rotator knob 572 to retract the delivery sleeve and thereby expose the prosthetic valve to the body vessel and effect deployment. The threading of the threaded portion 576 of the lead screw 506 acts on the internal threading of the lead screw nut 514, causing the lead screw nut 514 and the distal plate assembly 502 to translate toward the proximal plate assembly 504, which is held translationally stationary relative to the lead screw 506 by the snap rings 582. Thus, the distal and proximal plate assemblies 502, 504 move relative to each other, which causes the delivery sleeve 24, which is attached to the distal plate assembly 502 at the end piece 203 of the proximal hub 26, and the valve catheter 23, which is secured to the proximal plate assembly 504, to move relative to each other.

In the alternative embodiment shown in FIGS. 18 and 21 employing the alternative handle assembly 608, the operator turns the deployment knob 620 such that the knob 620, as well as the proximal hub 26 and delivery sleeve 24, which are connected to the deployment knob 620, travels proximally over the valve catheter 23.

The use of the lead screw 506 or the alternative handle assembly 608 potentially reduces the force needed to retract the delivery sleeve from the prosthetic valve 16. One complete revolution of the lead screw 506 advances the lead screw nut 514 the distance between the individual threads on the threaded portion 576 of the lead screw 506. The distance between threads, known as the pitch, determines the amount of force required by the operator to actuate the rotator knob 572. The smaller the pitch, the less the translational movement is achieved per revolution of the rotator knob 572. Less relative translational movement of the delivery sleeve 24 on one hand and the prosthetic valve and valve catheter 19 on the other hand, the less force required by the system operator. In a preferred embodiment of the present invention, the lead screw has a pitch of ¼ inch.

In an alternative embodiment of the present invention not employing a lead screw, the operator holds the valve catheter 23 steady and pulls back (proximally) on the proximal hub 26, which remains outside the body vessel, to expose the prosthetic valve to the body vessel and effectuate valve deployment.

Figure 23A:
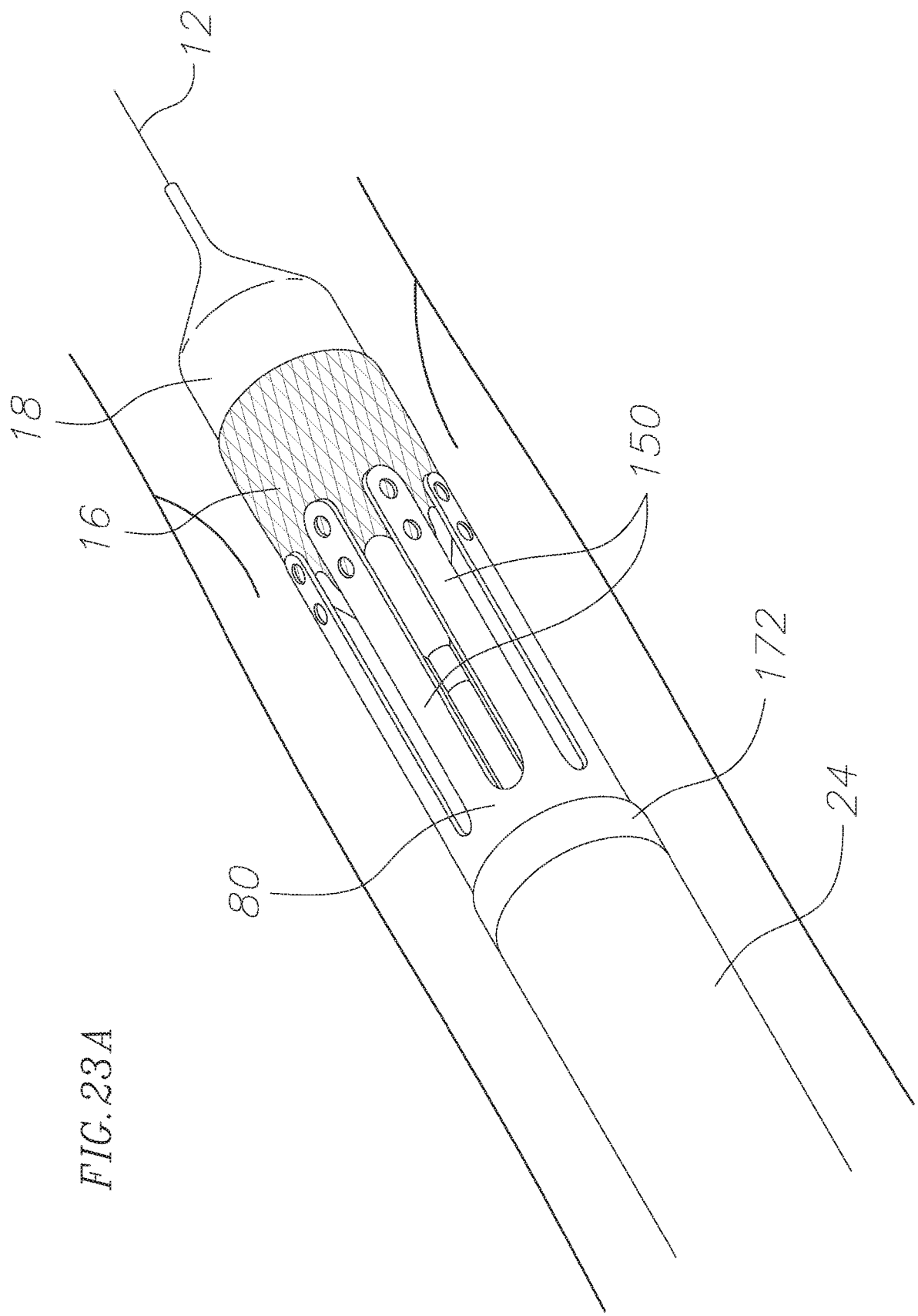
FIGS. 23A to 23E show a distal end portion of the delivery system during one preferred method of use for delivering and deploying a prosthetic valve.

With reference now to FIG. 23A, the delivery sleeve 24 is illustrated in the retracted position such that the prosthetic valve 16 and the extensions 150 of the mop 80 are exposed. The tip portion 172 of the delivery sleeve 24 is sufficiently flexible to allow retraction of the delivery sleeve 24 during valve deployment despite the pressure exerted on the delivery sleeve 24 by the expanding prosthetic valve. In order for the retraction of the delivery sleeve 24 to be more easily executed by the operator, the inner layer 173 of the delivery sleeve 24 (see FIG. 9) may be formed of a material with a low coefficient of friction, such as Teflon®.

Figure 23B:
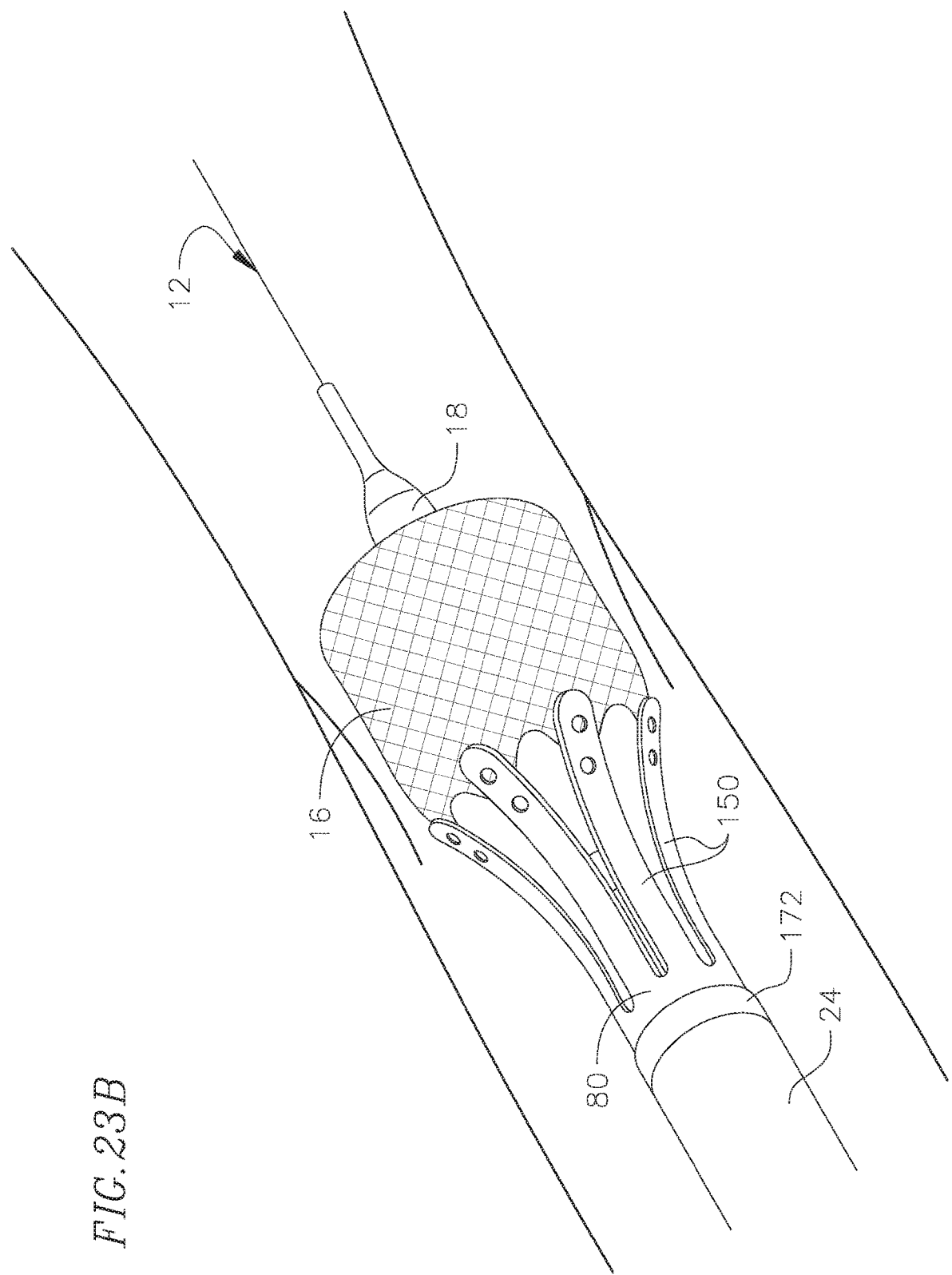
Figure 23C:
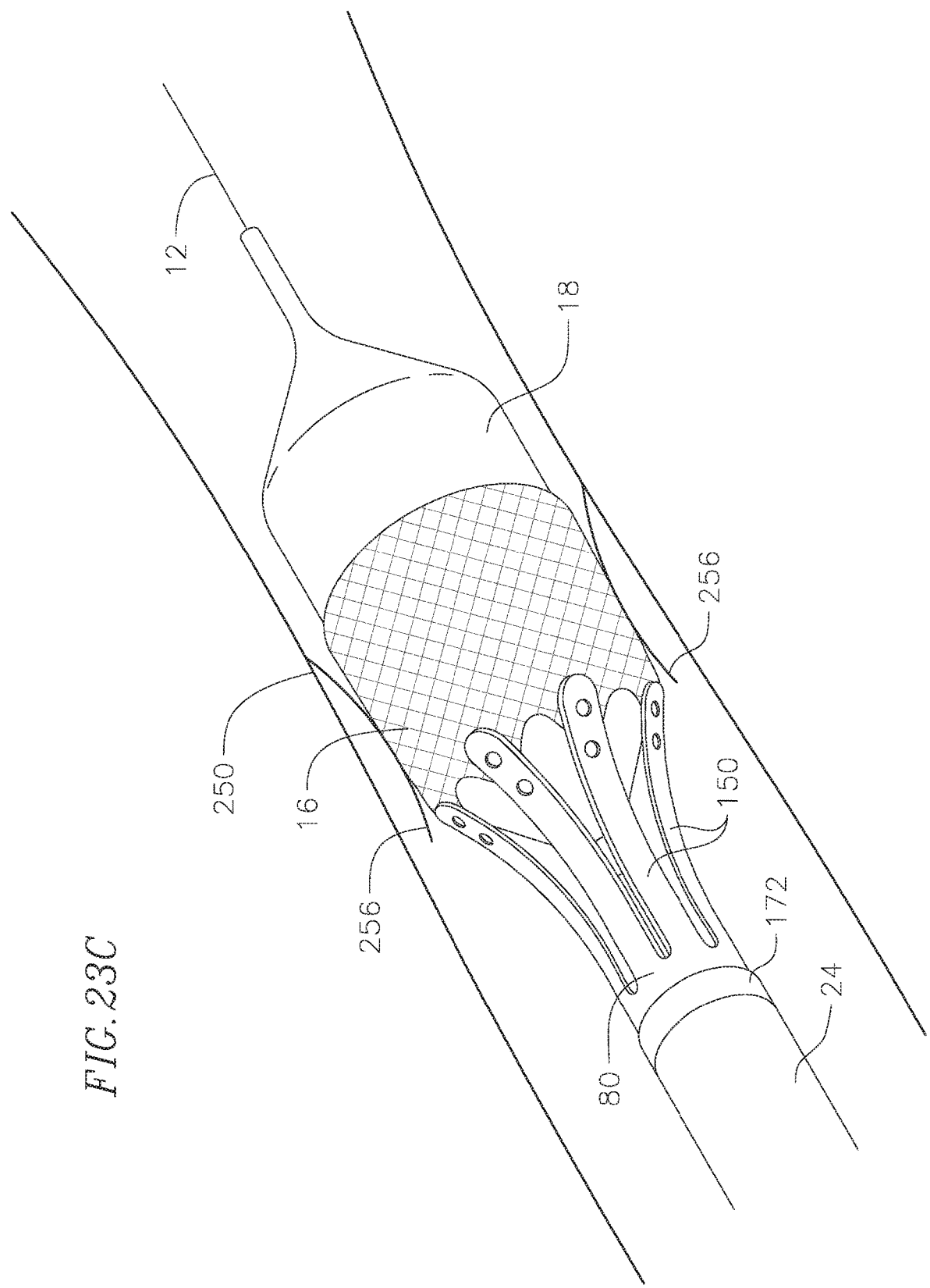

With reference to FIG. 23B, the balloon 18 can be deflated while the self-expanding capabilities of the prosthetic valve 16 cause it to expand outwardly. The extensions 15 of the mop 80 are preferably sufficiently flexible such that the extensions may allow expansion of the valve while maintaining the connection with the valve 16. With reference to FIG. 23C, after the prosthetic valve 16 has initially expanded, the balloon 18 may be inflated again to further increase the diameter of the prosthetic valve 16. The additional expansion ensures that the prosthetic valve assumes a fully expanded condition whereby the valve is securely seated at the site of the native valve 250. During expansion of the prosthetic valve, the leaflets 256 at the native valve site 250 are pressed against the wall of the aorta. As discussed above, the balloon 18 is inflated by a fluid source attached to the fluid shaft 34 of the support 22 of the balloon catheter 14 (see FIG. 2). The stop cock 35 controls the flow of fluid into the main shaft 32 and the balloon shaft 20 of the balloon catheter 14 (see FIG. 2). The compression valve of the Touhy Borst valve 36 prevents fluid leakage from the balloon catheter 14 (see FIG. 2).

The extensions 150 of the mop 80 flex outwardly to accommodate expansion of the prosthetic valve 16. During expansion of the prosthetic valve 16 as shown in FIGS. 23B and 23C, the operator can adjust the position of the prosthetic valve by advancing or retracting the valve catheter 23 of the delivery system 10. The extensions 150 of the mop 80 possess sufficient stiffness to allow the position of the prosthetic valve 16 to be manipulated with a minimum amount of control. Prior to valve deployment, control of valve positioning is achieved by the operator pushing, pulling, or twisting the valve catheter 23. The connection between the valve catheter 23 and the balloon catheter 14 allows for movement of the valve catheter 23 to be transmitted from the valve catheter 23 to the balloon catheter 14.

Figure 23D:
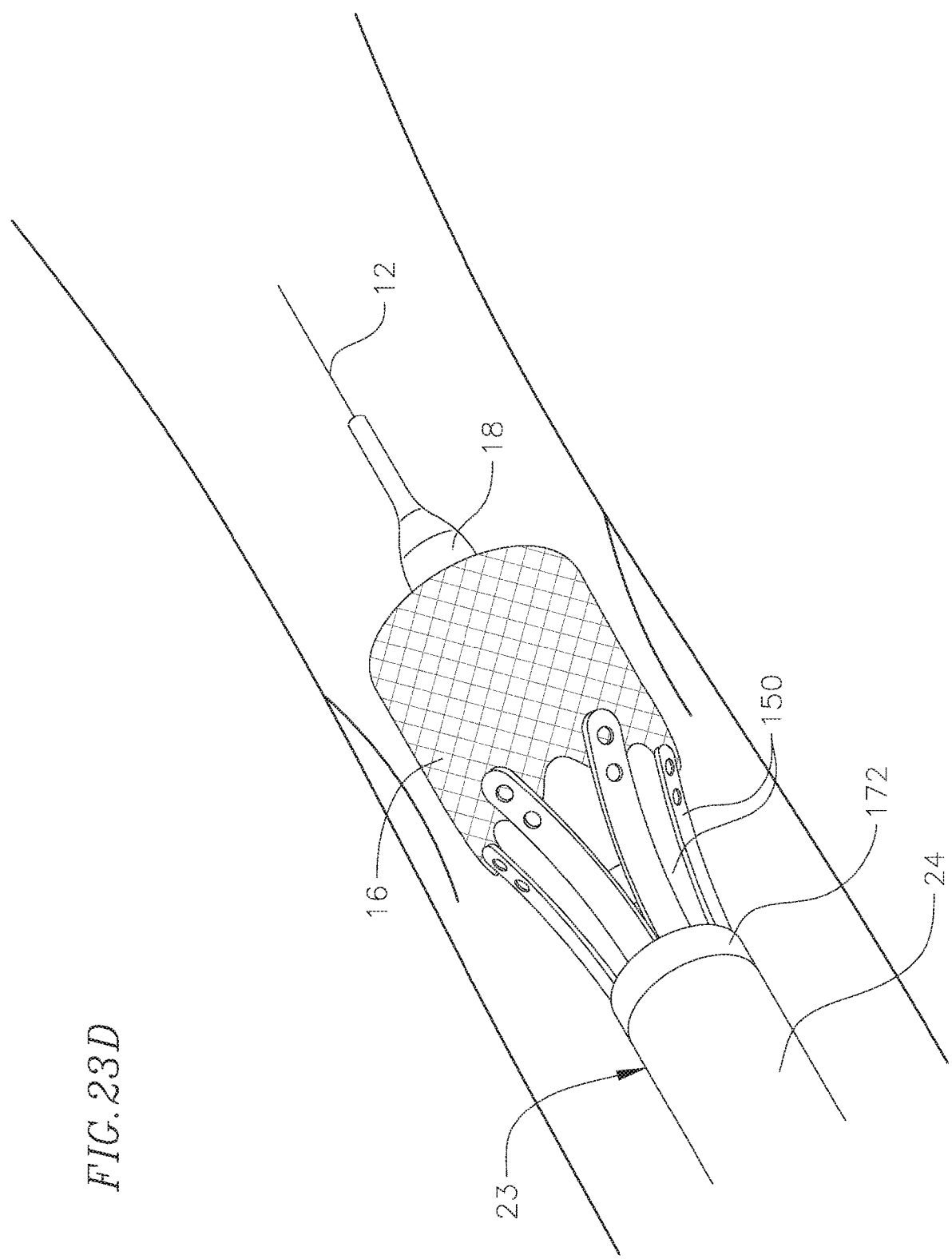

With reference to FIG. 23D, it is to be understood that the relative movement between the valve catheter 23 and the delivery sleeve 24 during valve deployment can be reversed, by reversing the direction of rotator knob 572 (or deployment knob 620) or by manually pushing (distally) the proximal hub 26 while holding the inner catheter 23 steady. In one advantageous feature, the delivery sleeve may be moved (i.e., advanced) relative to the valve catheter after initial deployment to reduce the diameter of the valve if the location and/or orientation of the valve is not desirable. More particularly, as the distal end 162 of the delivery sleeve 24 advances distally over the extensions 150 of the mop 80, the extensions 150 are pushed inwardly. As the extensions are pushed inwardly, the prosthetic valve is collapsed. Therefore, if the operator is not satisfied with the initial deployment of the prosthetic valve 16, the operator can collapse and reorient the prosthetic valve 16. As a result, the delivery system may be used to retract the prosthetic valve partially or entirely back into the delivery sleeve such that the prosthetic valve can be redeployed or withdrawn altogether.

Figure 23E:
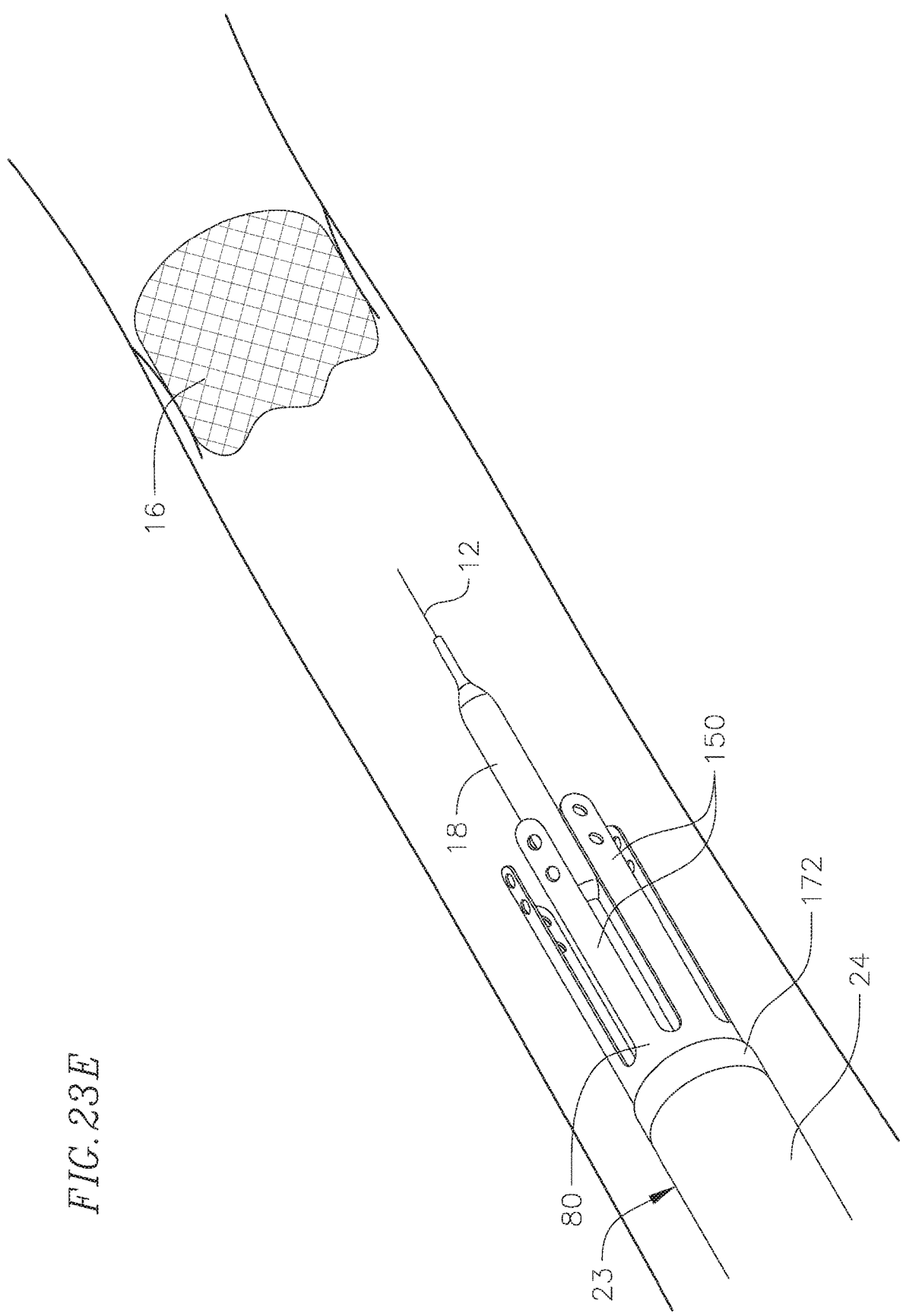

With reference to FIG. 23E, once the operator is satisfied with the position in which the prosthetic valve 16 is being seated, the prosthetic valve is detached from the extensions 150 of the mop 80. To disconnect the prosthetic valve 16 from the valve catheter 23, the pulls on the knob 236 connected to the bonded wire 234 (see FIG. 19). The distal ends of the six individual wires of the wire 234 are pulled from the commissure pockets and valve leaflets and from the suture 238, allowing the suture to exit the attachment point of the prosthetic valve 16 and thus freeing the suture 238 from the prosthetic valve 16 (see FIG. 20). The prosthetic valve 16 is then detached from the valve catheter 23. Detachment of the prosthetic valve 16 can occur at any time that the operator deems appropriate, but usually occurs when the extensions 150 have expanded outwardly to their fullest extent.

After releasing the prosthetic valve 16, the valve catheter 23 and balloon catheter 14 are preferably returned to the passageway 168 of the delivery sleeve 24 (see FIG. 11). To return the valve catheter 23 and balloon catheter 14 to the passageway 168 of the delivery sleeve 24 in those embodiments of the invention including the handle assemblies 500, 608 (see FIGS. 12 and 21), the operator reverses the direction of rotator knob 572 or deployment knob 620. In the alterative embodiment not employing a lead screw, the surgeon pulls (proximally) on the valve catheter 23 and balloon catheter 14 while holding the delivery sleeve 24 stationary (see FIG. 1). The delivery system 10 is then withdrawn from the body vessel of the patient.

Although preferred embodiments described herein include a balloon catheter which may be used as a dilator tip and may also be used to help seat the prosthetic valve, it will be appreciated that the system may be used without a balloon catheter. When no balloon catheter is provided, the prosthetic valve is released from the valve catheter and self-expands with sufficient force to firmly implant itself at the treatment site. In another variation of the preferred embodiments described herein, the delivery system may be configured such that the balloon catheter and the valve catheter form an integrated unit.

Figure 24:
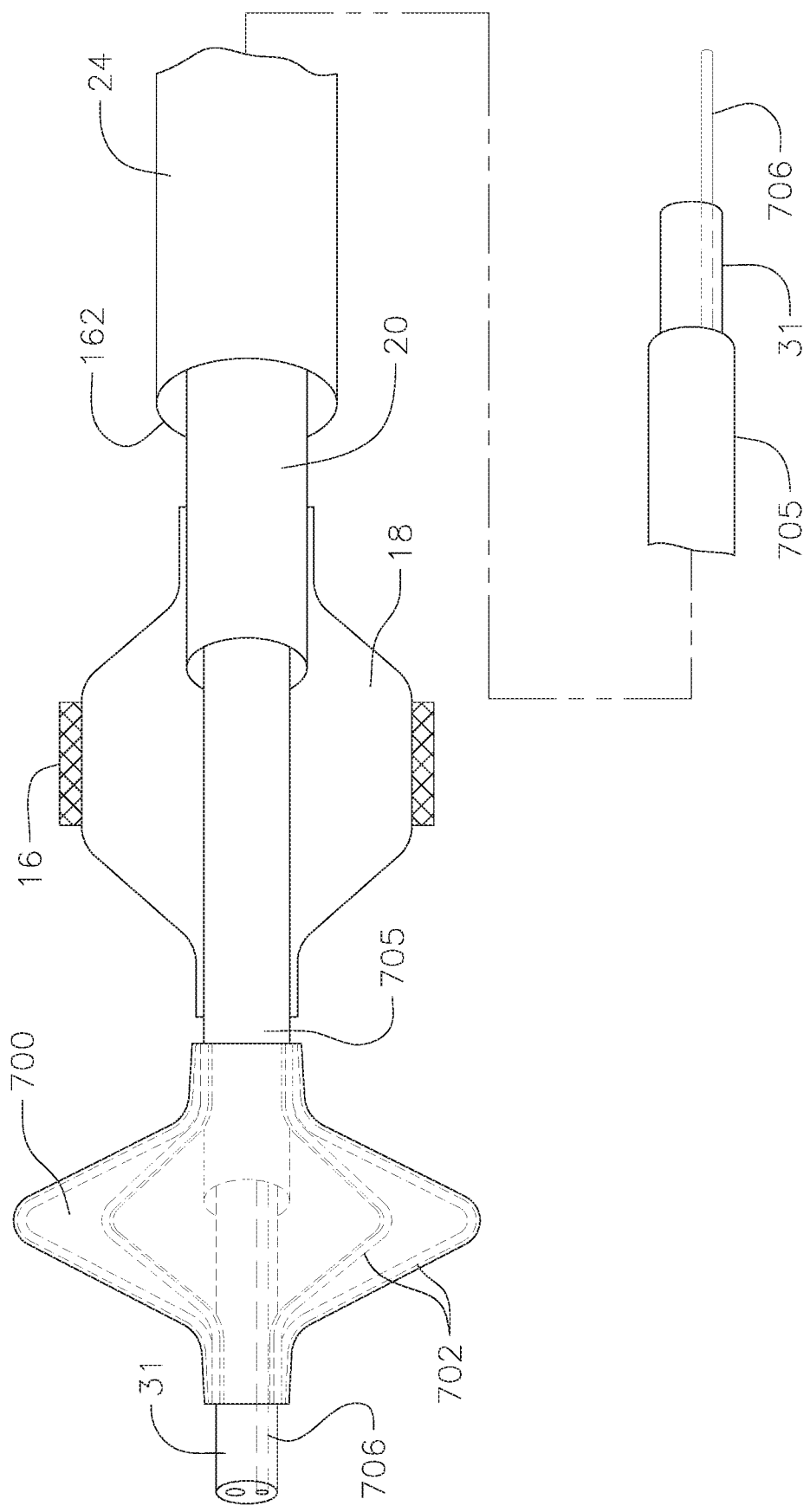
FIG. 24 is a side view of an alternative embodiment of the delivery system showing a mechanical basket tip.

With reference to FIG. 24, in another alternative embodiment, the transition member protruding distally from the delivery sleeve 24 may take the form of a mechanical basket 700 to facilitate entry into the body vessel and tracking to the native valve site. The mechanical basket includes struts 702 enveloped in a urethane covering 704, which is secured over the guidewire shaft 31 at a distal end and a basket shaft 705 at a proximal end. The struts 702 are formed with laser cut tubing. The struts can be heat set to flex outwardly, and preferably are formed of super elastic Nitinol in order to expand and collapse effectively. The urethane covering 704 provides a smooth rounded tip for tracking through the aorta. During tracking, the basket 700 protrudes from the distal end 162 of the delivery sleeve 24.

The basket shaft 705 passes through the balloon shaft 20. The balloon 18 is secured over the basket shaft 705 at the distal end 42 (see FIGS. 3A and 3B) and to the balloon shaft 20 at a proximal end 40 (see FIGS. 3A and 3B). The balloon shaft 20 passes through the delivery sleeve 24.

The guidewire shaft 31 protrudes distally from the basket shaft 705 and includes a pull wire 706 extending from a distal end of the guidewire shaft 31, where it is attached, through the basket, and to the proximal end of the delivery system 10, where it can be operated to expand or collapse the basket 700. The guidewire shaft 31 and basket shaft 705 pass through the delivery system 10 and protrude proximally from the support 22 (see FIG. 2). The basket shaft 705 protrudes proximally from the guidewire shaft 31. The guidewire shaft 31 and basket shaft 705 can move relative to each other as the operator holds the basket shaft 705 steady and pushes or pulls the guidewire shaft 31. The operator can also use the pull wire 706 to achieve relative movement between the guidewire shaft 31 and the basket shaft 705. Relative movement between the shafts 31, 705 at a distal end causes the struts 702 of the basket 700 to flex inwardly or outwardly as the distal and proximal end of the basket move away from or toward one another.

While tracking to the native valve site, the basket 700 protrudes distally from the distal end 162 of the delivery sleeve 24. The shape of the basket 700 provides a tapered surface for ease of transition into the body vessel, and for ease of tracking through the body vessel to the native valve site, similar to the balloon 18, as described above.

In the alternative embodiment shown in FIG. 24, relative movement between the guidewire shaft 31 and the basket shaft 705 is used to collapse and expand the struts 702 of the basket 700. The urethane covering 704 collapses with the struts 702. The mechanical basket 700 can be collapsed and expanded to loosen stenotic leaflets, or dilate constrictive portions of the body vessel. The prosthetic valve 16 can be placed on the balloon 18 and in the delivery sleeve 24, as in the other embodiments discussed herein, and valve deployment can occur similarly as in the other embodiments discussed herein.

While the invention has been described in its preferred embodiments, it is to be understood that the words which have been used are words of description and not of limitation. Therefore, changes may be made within the scope of the appended claims without departing from the true scope and spirit of the invention.

What is claimed is:

1. An assembly for treating a native valve in a human heart, comprising:
    a prosthetic heart valve including a proximal end portion, a distal end portion, an expandable frame, and a valvular structure;
    a tubular sleeve defining a passageway;
    a valve catheter disposed in the sleeve and having a proximal end portion and a distal end portion, the valve catheter and the sleeve configured to be advanced together through a body vessel to the heart;
    a plurality of metal extension arms coupled to the distal end portion of the valve catheter and releasably coupled to the proximal end portion of the prosthetic heart valve, wherein the extension arms are configured to hold the prosthetic heart valve, to radially expand with the prosthetic heart valve during expansion of the prosthetic heart valve at a treatment site, and to radially contract when relative movement between the sleeve and the valve catheter results in the extension arms being disposed within the sleeve; and
    a plurality of metal rods extending distally from the distal end portion of the valve catheter, wherein the rods are releasably coupled to the proximal end portion of the prosthetic heart valve and are axially movable relative to the extension arms.

2. The assembly of claim 1, wherein the extension arms are circumferentially spaced relative to each other, and wherein each rod is circumferentially aligned with a respective extension arm.

3. The assembly of claim 1, further comprising a plurality of release members coupled to the distal end portion of the valve catheter, wherein each of the release members is moveable between a first state and a second state, wherein when the release members are in the first state, each release member extends through a respective aperture of the prosthetic heart valve, thereby releasably retaining the prosthetic heart valve on the rods and the extension arms, and wherein when the release members are in the second state, each release member is removed from its respective aperture, thereby allowing the prosthetic heart valve to be released from the rods and the extension arms.

4. The assembly of claim 1, further comprising a base extending into an opening of the distal end portion of the valve catheter, wherein proximal end portions of the extension arms are coupled to the base.

5. The assembly of claim 1, further comprising a handle portion having an actuation mechanism and a knob, and the sleeve and the valve catheter are adjustably coupled to the actuation mechanism, wherein rotating the knob relative to the valve catheter actuates the actuation mechanism, thereby causing relative axial movement between the sleeve and the valve catheter.

6. The assembly of claim 5, wherein the actuation mechanism includes a lead screw coupled to the knob.

7. The assembly of claim 5, wherein the knob of the handle portion is a first knob, and the handle portion further comprises a second knob, wherein the rods are coupled to the second knob, and movement of the second knob relative to the valve catheter causes the rods to move axially relative to the prosthetic heart valve and the extension arms, wherein the first knob is rotatable relative to the valve catheter, and the second knob is moveable relative to the valve catheter.

* * * * *